(12) United States Patent
Sachs

(10) Patent No.: US 11,229,414 B2
(45) Date of Patent: Jan. 25, 2022

(54) ADJUSTABLE DETECTOR ARRAY FOR A NUCLEAR MEDICINE IMAGING SYSTEM

(71) Applicant: GE Precision Healthcare LLC, Milwaukee, WI (US)

(72) Inventor: Jonathan Sachs, Haifa (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 178 days.

(21) Appl. No.: 16/747,268

(22) Filed: Jan. 20, 2020

(65) Prior Publication Data
US 2021/0219931 A1    Jul. 22, 2021

(51) Int. Cl.
*A61B 6/00* (2006.01)
*A61B 6/06* (2006.01)
*A61B 6/04* (2006.01)

(52) U.S. Cl.
CPC .......... *A61B 6/4266* (2013.01); *A61B 6/0487* (2020.08); *A61B 6/06* (2013.01); *A61B 6/547* (2013.01)

(58) Field of Classification Search
CPC ..... A61L 6/4266; A61L 6/4014; A61L 6/4275
See application file for complete search history.

(56) References Cited

U.S. PATENT DOCUMENTS

| | | | |
|---|---|---|---|
| 9,442,197 B2 | 9/2016 | Shahar | |
| 9,554,489 B2 | 1/2017 | Hefetz et al. | |
| 9,662,079 B2 | 5/2017 | Rafaeli et al. | |
| 10,148,133 B2 | 12/2018 | Leabman et al. | |
| 2015/0094574 A1 | 4/2015 | Bouhnik et al. | |
| 2016/0022228 A1* | 1/2016 | Khen | G06T 11/005 |
| | | | 250/363.05 |

OTHER PUBLICATIONS

Bouhnik, J., "Adjustable Detector Array for a Nuclear Medicine Imaging System," U.S. Appl. No. 16/747,155, filed Jan. 20, 2020, 45 pages.
Bouhnik, J., "Adjustable Detector Array for a Nuclear Medicine Imaging System," U.S. Appl. No. 16/747,191, filed Jan. 20, 2020, 46 pages.

* cited by examiner

*Primary Examiner* — Dani Fox
(74) *Attorney, Agent, or Firm* — McCoy Russell LLP

(57) ABSTRACT

Methods and systems are provided for a medical imaging system having a detector array. In one example, the detector array may include a plurality of adjustable imaging detectors, each of the plurality of adjustable imaging detectors including a first detector unit or a second detector unit, each first detector unit having a plurality of rows of detector modules and each second detector unit having at least one row of detector modules, wherein each second detector unit may have fewer rows of detector modules than each first detector unit, the plurality of adjustable imaging detectors may be arranged on an annular gantry, the annular gantry configured for rotation about an axis of a cylindrical aperture of the annular gantry, the axis extending a length of the cylindrical aperture, and each of the plurality of adjustable imaging detectors may be disposed within the cylindrical aperture and may extend orthogonally toward the axis.

20 Claims, 12 Drawing Sheets

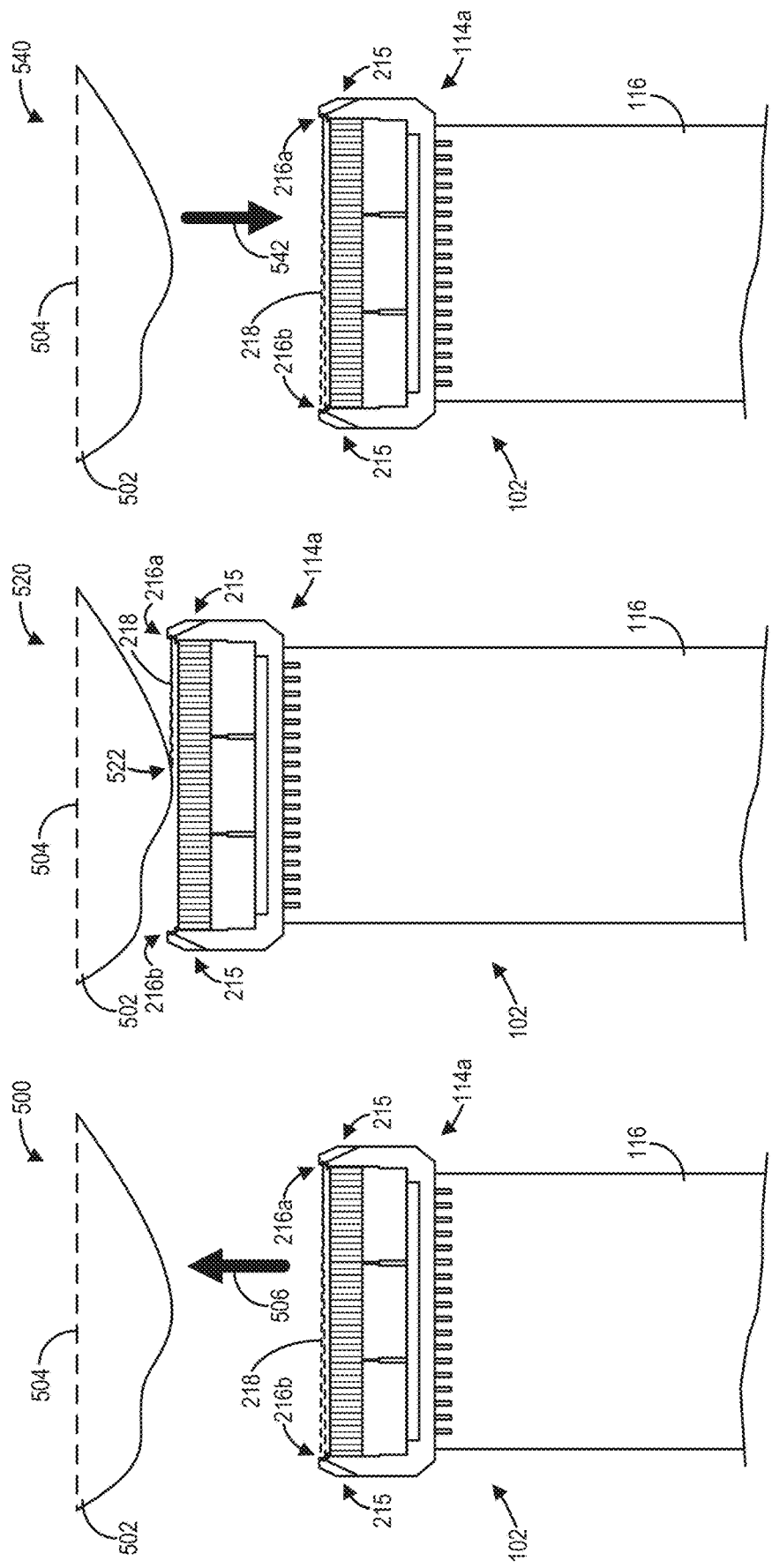

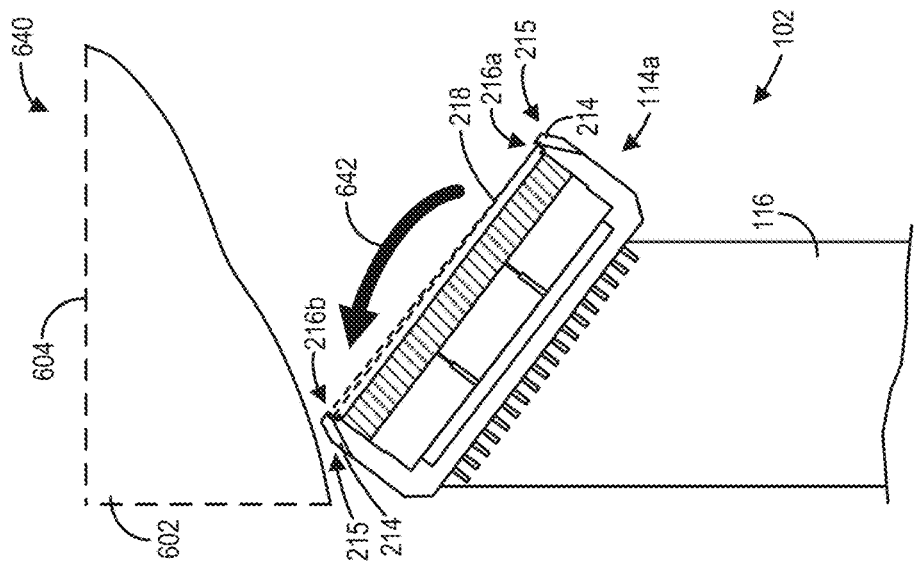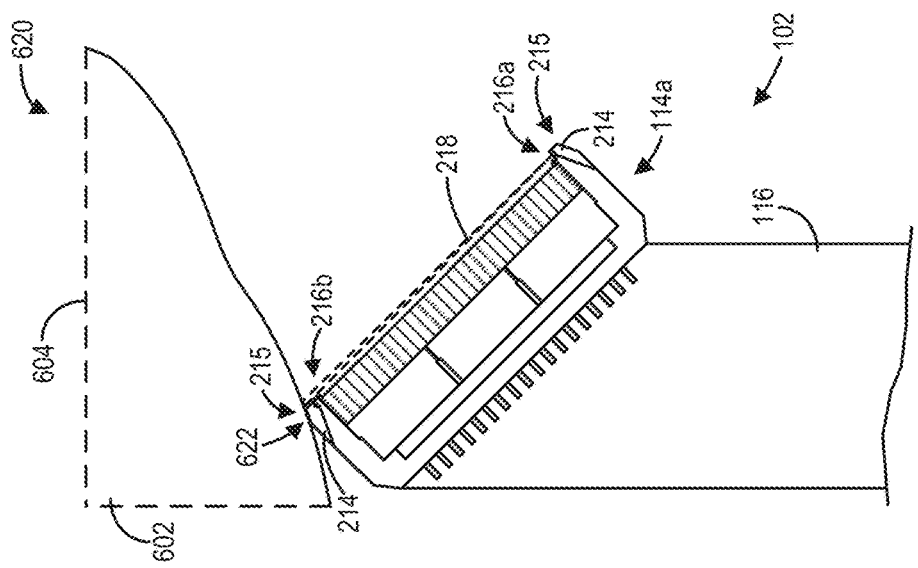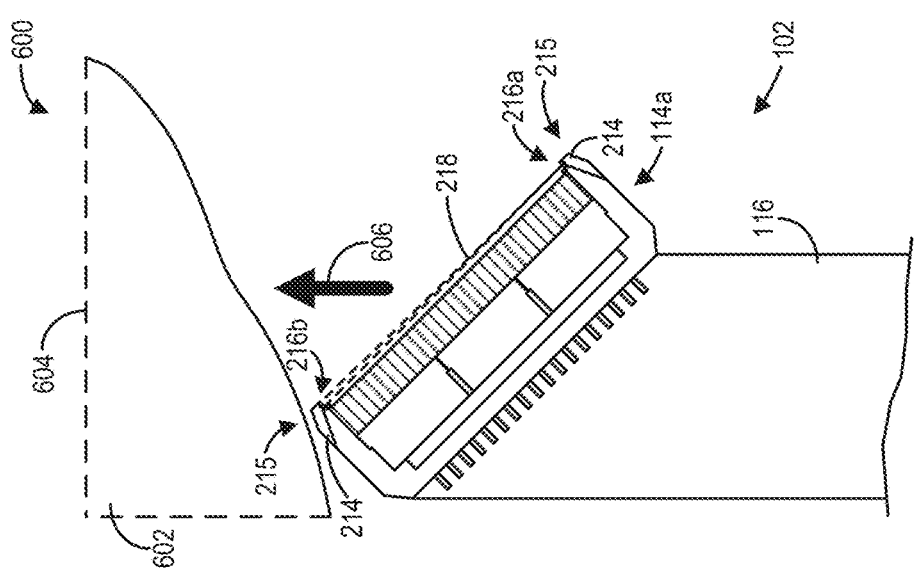

ADJUSTABLE DETECTOR ARRAY FOR A NUCLEAR MEDICINE IMAGING SYSTEM

FIELD

Embodiments of the subject matter disclosed herein relate to medical imaging systems, and more particularly to an adjustable detector array for nuclear medicine imaging systems.

BACKGROUND

Nuclear medicine (NM) imaging systems may include multiple detectors or detector heads for imaging a subject, such as a patient. For example, the detectors may be positioned adjacent to the subject on a gantry to acquire NM imaging data (e.g., radioactivity) with a wide field of view. The acquired NM imaging data may then be used to generate a three-dimensional (3D) image of the subject. Some NM imaging systems may have moving detector heads, such as gamma cameras, positioned to focus on a region of interest. One or more of the gamma cameras may be moved (for example, rotated) to different angular positions to acquire the NM imaging data. In one example, a detector array may include a plurality of detectors dispersed around the gantry, which may each be moved (e.g., translated and/or rotated) in close proximity to the subject to increase an imaging sensitivity. However, the close proximity may present physical (e.g., pinching) or mental (e.g., claustrophobia) discomfort for the subject. Further, the imaging sensitivity may be fundamentally limited by a specific configuration of cadmium zinc telluride (CZT) modules included in each detector. For example, each detector may include a single row of CZT modules.

BRIEF DESCRIPTION

In one embodiment, a detector array may include a plurality of adjustable imaging detectors, each of the plurality of adjustable imaging detectors including one of a first detector unit and a second detector unit, each first detector unit having a plurality of rows of detector modules and each second detector unit having at least one row of detector modules, where each second detector unit may have fewer rows of detector modules than each first detector unit, wherein the plurality of adjustable imaging detectors may be arranged on an annular gantry, the annular gantry configured for rotation about an axis of a cylindrical aperture of the annular gantry, the axis extending a length of the cylindrical aperture, and wherein each of the plurality of adjustable imaging detectors may be disposed within the cylindrical aperture and may extend orthogonally toward the axis.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 5A-5C show schematic diagrams illustrating a first exemplary process for adjusting a position of the imaging detector including the first detector unit, according to an embodiment;

FIGS. 6A-6C show schematic diagrams illustrating a second exemplary process for adjusting the position of the imaging detector including the first detector unit, according to an embodiment;

DETAILED DESCRIPTION

Figure 1:
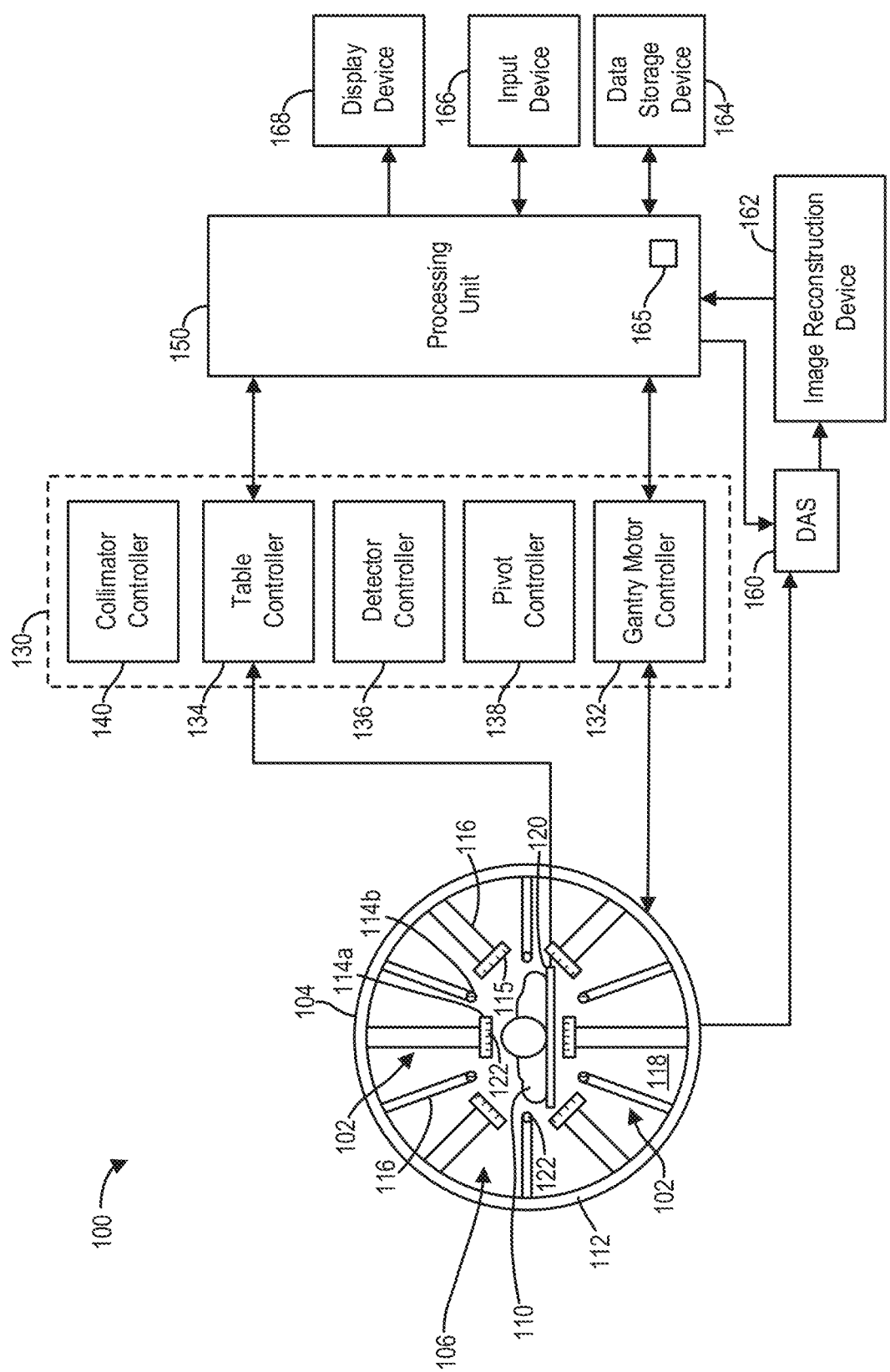
FIG. 1 shows a schematic block diagram of a nuclear medicine (NM) imaging system, according to an embodiment.

The following description relates to various embodiments of nuclear medicine (NM) imaging systems, and adjustable detector array configurations therefor. One example NM imaging system employing an exemplary detector array is depicted in FIG. 1. The detector array may include a plurality of imaging detectors, each of the plurality of imaging detectors including a respective detector unit. Each detector unit may either be a first detector unit having multiple rows of cadmium zinc telluride (CZT) modules, such as the detector unit depicted in FIG. 2A, or a second detector unit having a single row of CZT modules, such as the detector unit depicted in FIG. 2B. Various configurations of the detector array having varying numbers of first and second detector units are provided in FIGS. 7A-7D.

Figure 3A:
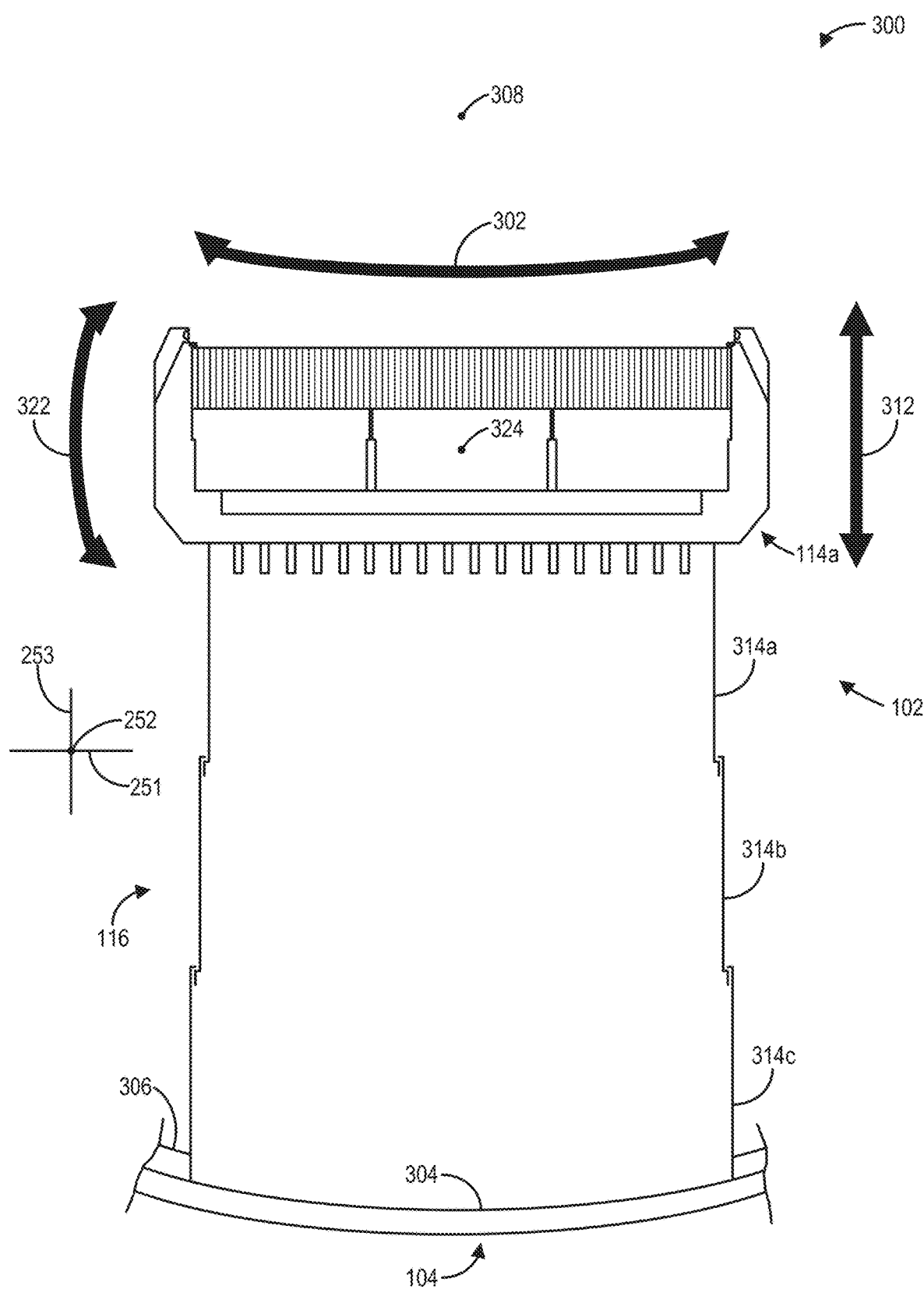
FIG. 3A shows a schematic diagram illustrating various movements of an imaging detector including the first detector unit, according to an embodiment.
Figure 3B:
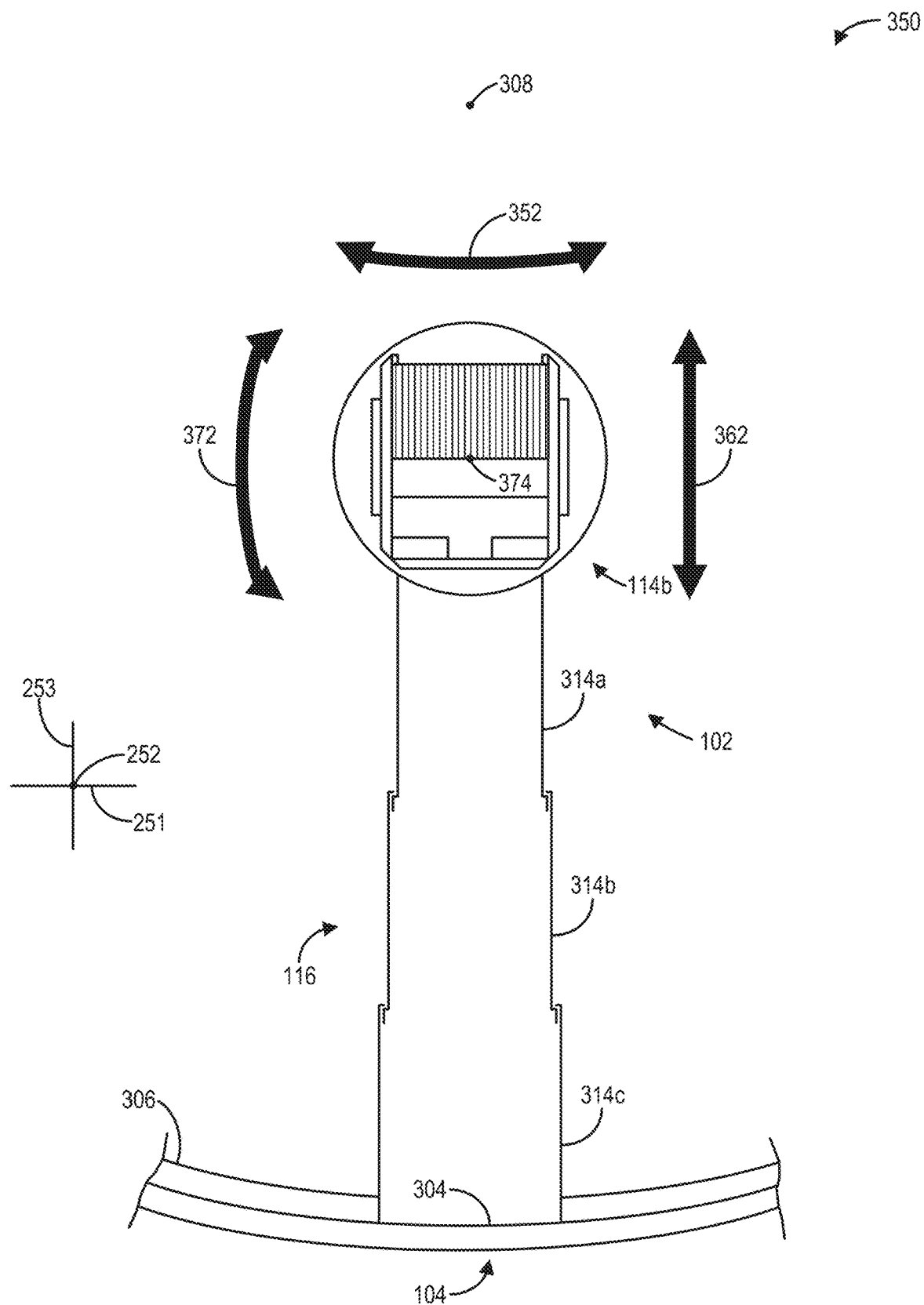
FIG. 3B shows a schematic diagram illustrating various movements of an imaging detector including the second detector unit, according to an embodiment.
Figure 4B:
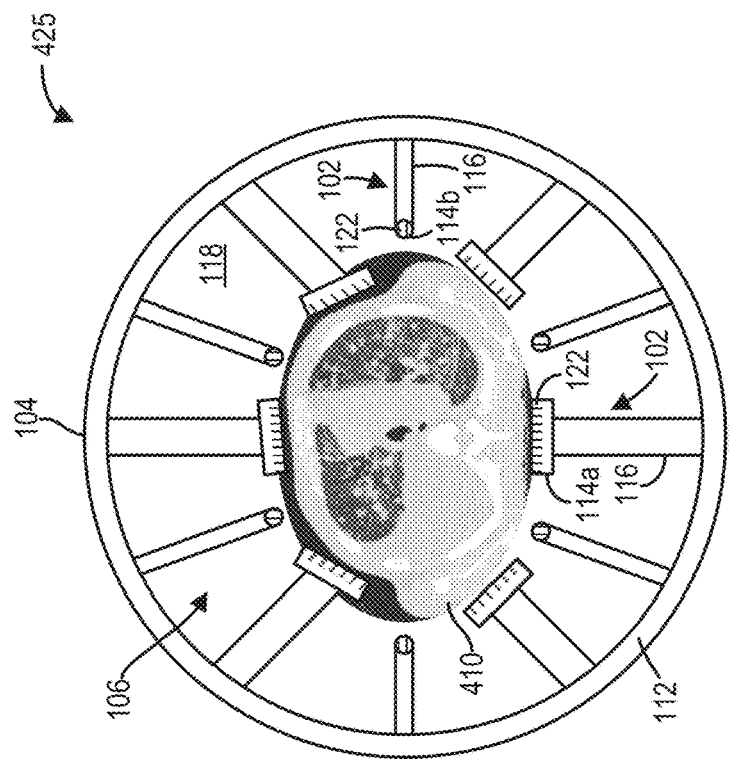
FIGS. 4A and 4B show schematic diagrams illustrating a first exemplary process for a detector array of the NM imaging system conforming to a subject to be imaged, according to an embodiment.
Figure 4A:
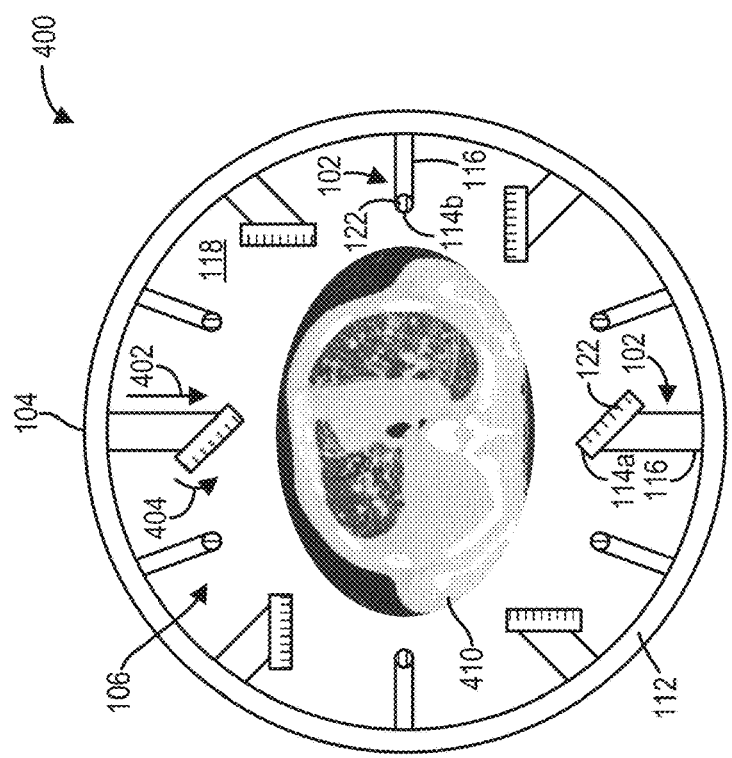
Figure 4D:
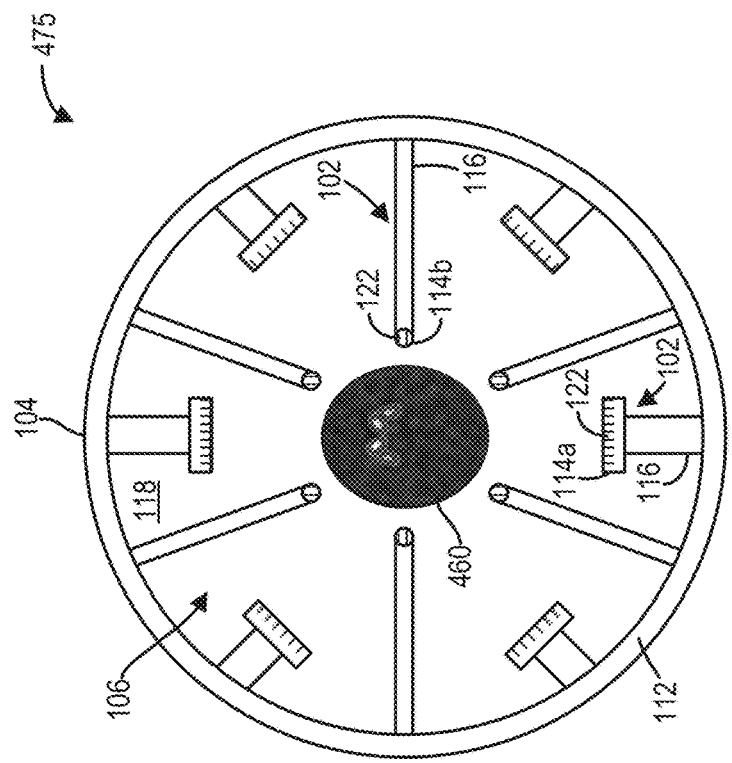
FIGS. 4C and 4D show schematic diagrams illustrating a second exemplary process for conforming the detector array of the NM imaging system to the subject to be imaged, according to an embodiment.
Figure 4C:
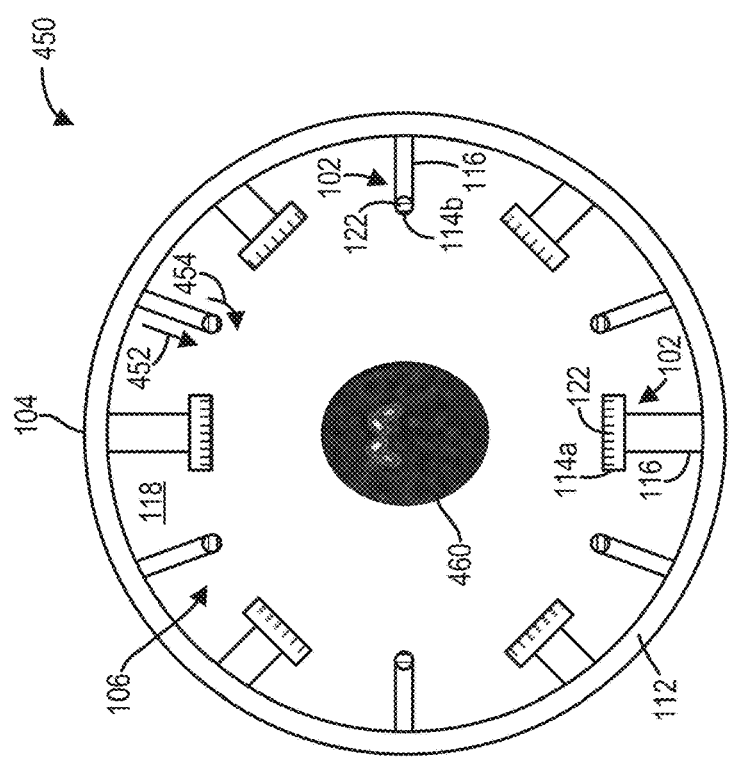
Figure 7A:
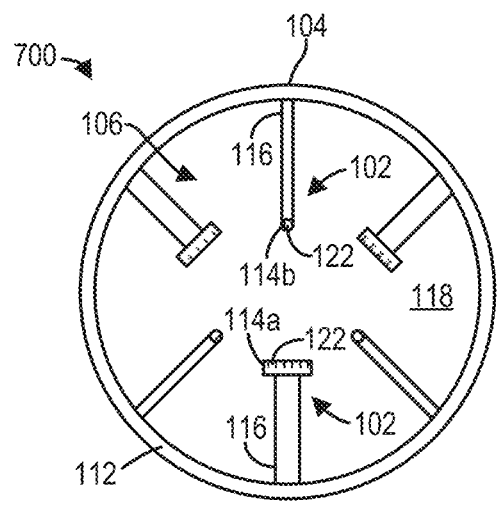
FIGS. 7A-7D show schematic diagrams illustrating exemplary configurations of the detector array, according to an embodiment.
Figure 7B:
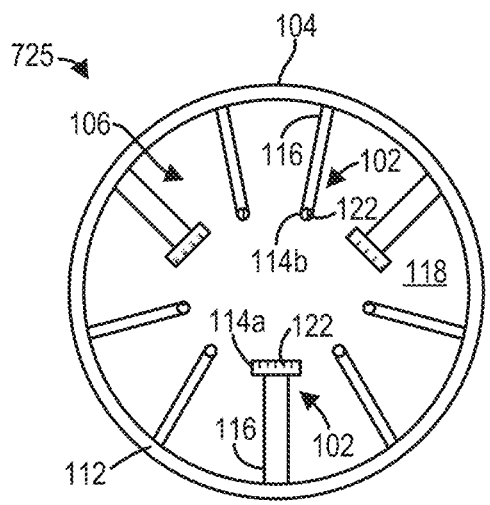
Figure 7C:
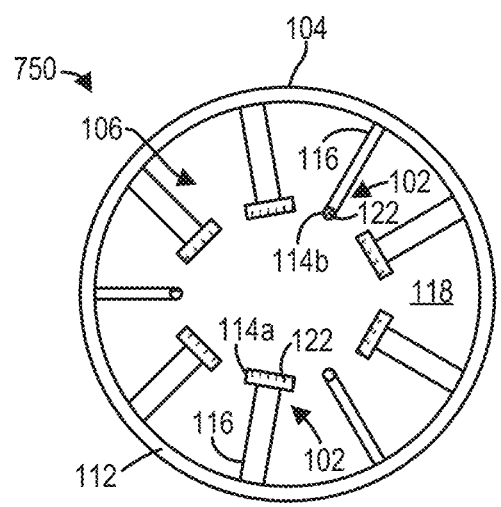
Figure 7D:
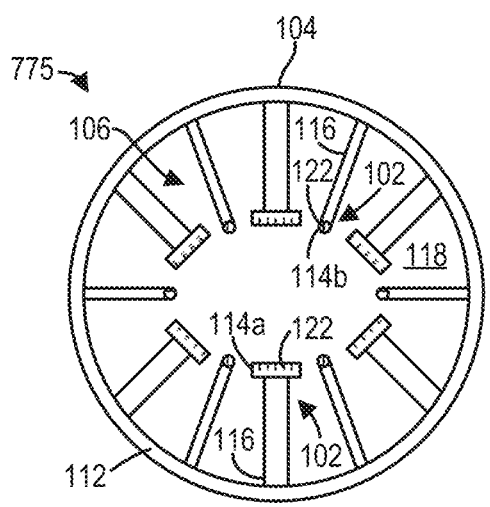

The first detector unit may move around one axis of rotation and one pivoting axis, and along one axis of translation, as depicted in FIG. 3A, so as to conform to a subject to be imaged by the NM imaging system, an exemplary process for which is depicted in FIGS. 4A and 4B. The second detector unit may move around one axis of rotation and one pivoting axis, and along one axis of translation in a similar fashion, as depicted in FIG. 3B; a similar exemplary process for conforming the second detector units to the subject to be imaged is depicted in FIGS. 4C and 4D. To mitigate discomfort to the subject and undue pressure to the detector unit, each detector unit may be provided with various sensors. As a first example, and as shown in FIGS. 5A-5C, a pair of optical sensors may be included in the first detector unit and may project light from a light-emitting diode (LED) therebetween, such that when an object (e.g., the subject to be imaged) obscures or obstructs the LED light, the first detector unit may retract. As a second example, and as shown in FIGS. 6A-6C, a pair of pressure-based sliding-end contact sensors may also be included in the first detector unit and may trigger pivoting of the first detector unit away from an object (e.g., the subject to be imaged) when one of the sliding-end contact sensors is contacted and actuated by the object.

The detector array, and the individual detector units therein, may be controlled via a controller unit of the NM imaging system to conform to an outer perimeter of the subject to be imaged. Exemplary routines which may be implemented include the methods provided in FIGS. 8 and 9 for imaging the subject with sufficient angular resolution and positioning the first and second detector units therefor.

FIG. 1 is a schematic illustration of a NM imaging system 100 having a plurality of imaging detectors mounted on a gantry. The imaging detectors may be configured to rotate around a fixed pivot. The movement of the imaging detectors may be controlled to reduce the likelihood of, or avoid, collision among the moving imaging detectors and/or reduce the likelihood of one imaging detector obstructing the field of view of another imaging detector. For example, the NM imaging system in some embodiments provides coordinated swinging or pivoting motion of a plurality of imaging detectors or detector units therein.

In particular, a plurality of imaging detectors 102 are mounted to a gantry 104 and/or a patient support structure (not shown) (e.g., under a patient table 120), which may define a table support for the patient table 120. In the illustrated embodiment, the imaging detectors 102 are configured as a detector array 106 positioned around the subject 110 (e.g., a patient), as viewed in FIG. 1. The detector array 106 may be coupled directly to the gantry 104, or may be coupled via support members 112 thereto, to allow movement of the entire detector array 106 relative to the gantry 104 (e.g., rotational movement in the clockwise or counterclockwise direction as viewed in FIG. 1). Additionally, each of the imaging detectors 102 may include either a first, larger detector unit 114a or a second, smaller detector unit 114b, each of which may be mounted to a movable detector carrier 116 (e.g., a support arm or actuator that may be driven by a motor to cause movement thereof) that extends from the gantry 104. In imaging detectors 102 including the first detector units 114a, each of the first detector units 114a may be positioned outside of (e.g., at an end of) a respective detector carrier 116 nearest a center of an aperture 118 of the gantry 104. Conversely, in imaging detectors 102 including the second detector units 114b, each of the second detector units 114b may be positioned within (e.g., within an end of) a respective detector carrier 116 nearest the center of the aperture 118 of the gantry 104.

As shown, in some embodiments, the imaging detectors 102 including the first detector units 114a may alternate with the imaging detectors 102 including the second detector units 114b. However, it will be appreciated that many configurations of the first detector units 114a and the second detector units 114b may be contemplated and implemented within the scope of the present disclosure. In some embodiments, the smaller detector units 114b may retract such that the larger, higher-resolution detector units 114a may conform to and image smaller subjects 110. In additional or alternative embodiments, the larger detector units 114a may retract to provide space for imaging larger subjects 110 and the smaller detector units 114b may fill in gaps between the retracted larger detector units 114a. In this way, a given configuration of larger detector units 114a and smaller detector units 114b may be selected so as to provide flexible imaging of subjects 110 of varying sizes and shapes.

In some embodiments, the detector carriers 116 may allow movement of the detector units 114a, 114b toward and away from the subject 110, such as linearly. Thus, in the illustrated embodiment, the detector array 106 is around the subject 110 and may allow linear movement of the detector units 114a, 114b, such as toward or away from the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114a, 114b relative to the support member 112 and/or gantry 104, which in various embodiments allows the detector units 114a, 114b to move linearly toward and away from the support member 112, such as radially inward and outwards for positioning adjacent the subject 110. For example, as described herein, the detector units 114a, 114b may be controlled to move independently of each other toward or away from the subject 110, as well as capable of rotational, pivoting, or tilting movement in some embodiments.

Each of the imaging detectors 102 in various embodiments may be smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114a or 114b coupled to respective detector carrier(s) 116 and having dimensions of 4 cm to 32 cm and may be formed of a plurality of CZT tiles or modules. As an example, each of the first detector units 114a may be 16×32 cm in size and may be composed of 21 CZT pixelated modules (not shown at FIG. 1). As another example, each of the second detector units 114b may be 6×32 cm in size and be composed of a plurality of CZT pixelated modules (not shown). Further, in the first detector units 114a and/or the second detector units 114b, each module may be 4×4 cm in size and have 16×16 (=256) pixels, for example. In some embodiments, each larger detector unit 114a may include a plurality of modules, such as a multi-rowed array of 3×8 modules, 2×8 modules, 3×7 modules, or 2×7 modules, for example. In such embodiments, each smaller detector unit 114b may also include a plurality of modules, such as a single-rowed array of 1×7 modules, for example. In some embodiments, each larger detector unit 114a may include a plurality of rows of modules and each smaller detector unit 114b may include at least one row of modules, where each smaller detector unit 114b may have fewer rows of modules than each larger detector unit 114a. In a specific embodiment, each smaller detector unit 114b may include only one row of modules. However, different configurations and array sizes may be contemplated without departing from the scope of the present disclosure.

It should be understood that the imaging detectors 102 and/or the first detector units 114a and/or the second detector units 114b may be different sizes and/or shapes with respect to each other, such as square, rectangular, circular, or another shape. An actual field of view (FOV) of each of the imaging detectors 102 may be directly proportional to the size and shape of the respective imaging detector 102 and detector unit 114a, 114b. In some embodiments, each of the imaging detectors 102 having the first detector unit 114a may have a same configuration as each other imaging detector 102 having the first detector unit 114a. Thus, in such embodiments, each of the first detector units 114a may have a same configuration as each other first detector unit 114a. In additional or alternative embodiments, each of the imaging detectors 102 having the second detector unit 114b may have a same configuration as each other imaging detector 102 having the second detector unit 114b. Thus, in such embodiments, each of the second detector units 114b may have a same configuration as each other second detector unit 114b. In one embodiment, each of the first detector units 114a may have a rectangular shape, such that each CZT module in a given row of CZT modules may be equidistant from a surface 115 of a given first detector unit 114a. In an additional or alternative embodiment, each of the second detector units 114b may have a rectangular shape or a substantially spherical shape.

It will be appreciated that a number of imaging detectors 102 may vary between embodiments and is only to be limited by practical constraints and not by the exemplary embodiments discussed in the present disclosure. A lower limit of the number of imaging detectors 102 may be selected to provide a threshold amount of imaging coverage. An upper limit of the number of imaging detectors may be selected to prevent any given imaging detector 102 obscuring the FOV of another imaging detector 102. In exemplary embodiments, 2, 3, 4, 5, 6, 7, 8, 9, 10, 11, or 12 imaging detectors 102 may be included in the detector array 106. In some embodiments, a number of imaging detectors 102 including detector units 114a may be equal to a number of imaging detectors 102 including detector units 114b (e.g., 6 detector units 114a and 6 detector units 114b, 3 detector units 114a and 3 detector units 114b, etc.). In other embodiments, the number of imaging detectors 102 including detector units 114a may be greater than the number of imaging detectors 102 including detector units 114b (e.g., 6 detector units 114a and 3 detector units 114b, etc.). In other embodiments, the number of imaging detectors 102 including detector units 114a may be less than the number of imaging detectors 102 including detector units 114b (e.g., 3 detector units 114a and 6 detector units 114b, etc.).

The gantry 104 may be formed with the aperture 118 (e.g., cylindrical opening or bore) therethrough as illustrated. The patient table 120 may be configured with a support mechanism, such as the patient support structure, to support and carry the subject 110 in one or more of a plurality of viewing positions within the aperture 118 and relative to the imaging detectors 102. Alternatively, the gantry 104 may include a plurality of gantry segments (not shown), each of which may independently move a given support member 112 or one or more of the imaging detectors 102.

The gantry 104 may also be configured in other shapes, such as a "C," "H," or "L," for example, and may be rotatable about the subject 110. For example, the gantry 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry 104 may be arc-shaped and the support members 112 movable along the arc to position the imaging detectors 102 at different locations along the gantry 104. In some embodiments, the imaging detectors 102 may also be independently movable along the gantry 104.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head-to-toe direction of the subject 110), image data specific for a larger FOV may be acquired more quickly.

Each of the detector units 114a, 114b may include a radiation detection face, which may be directed toward the subject 110 or a region of interest within the subject 110. The radiation detection faces may each be covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel-hole collimator. However, other types of collimators, such as converging or diverging collimators may optionally or alternatively be used. Other examples for the collimator 122 include slanthole, pinhole, parallel-beam converging, diverging fan-beam, converging or diverging cone-beam, multi-bore converging, multi-bore converging fan-beam, multi-bore converging cone-beam, multi-bore diverging, or other types of collimators.

The detector units 114a, 114b may be configured such that a given collimator 122 may be exchanged for another collimator, e.g., to suit a different application. For example, a slanthole collimator may be used to direct radiation to and from an organ partially blocked from view. As another example, a pinhole collimator may be used to image a relatively small structure, such as a thyroid or a joint. In some embodiments, a given detector unit 114a, 114b may be fit with one type of collimator 122 and another detector unit 114a, 114b may be fit with another type of collimator 122. It will therefore be appreciated that many configurations of collimators 122 may be contemplated and implemented within the scope of the present disclosure. In this way, a breadth of imaging applications may be increased by varying types and configurations of collimators 122 in the detector units 114a, 114b.

Optionally, multi-bore collimators may be constructed to be registered with pixels of the detector units 114a, 114b, which in one embodiment are CZT detectors. However, other materials may be used. Registered collimation may improve spatial resolution by forcing photons going through one bore to be collected primarily by one pixel. Additionally, registered collimation may improve a sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator. Further, in some embodiments, the detector units 114a, 114b may not be fit to external covers. As such, the detector units 114a, 114b may move such that a surface thereof is as close as possible to the subject 110, thereby increasing an imaging sensitivity of the NM imaging system 100. As a result, however, a pivoting motion of the detector units 114a, 114b may be limited in some embodiments to avoid or limit contact with the subject 110.

In some embodiments, the larger detector units 114a may each be provided with a plurality of proximity detectors (not shown at FIG. 1, but described in detail below with reference to FIG. 2A). Each of the plurality of proximity detectors may include respective pressure sensors, optical sensors, capacitive sensors, and/or ultrasound sensors disposed at each corner of the surface 115. Feedback from a sensor included in a given larger detector unit 114a may indicate that the given larger detector unit 114a is within a threshold distance of the subject 110, the patient table 120, or another detector unit 114a, 114b, and the given larger detector unit 114a may automatically retract or otherwise move. In additional or alternative embodiments, an LED beam may be projected between the pair of sensors. In such embodiments, if the LED beam is interrupted, the corresponding larger detector unit 114a may automatically retract or otherwise move (as described in detail below with reference to FIGS. 5A-6C). In additional or alternative embodiments, automatic body contouring may be implemented via optical feedback, such that an outer perimeter of the subject 110 may be approximated and the detector units 114a, 114b may automatically avoid the subject 110.

A controller unit 130 may control the movement and positioning of the patient table 120, imaging detectors 102, gantry 104, and/or the collimators 122. A range of motion before or during an acquisition, or between different image acquisitions, is set to maintain the actual FOV of each of the imaging detectors 102 directed, for example, toward or "aimed at" a particular area or region of the subject 110 or along the entire subject 110.

The controller unit 130 may have a gantry motor controller 132, table controller 134, detector controller 136, pivot controller 138, and collimator controller 140. The controllers 132, 134, 136, 138, 140 (that is, the controller unit 130) may be automatically commanded by a processing unit 150, manually controlled by an operator, or a combination thereof. The gantry motor controller 132 may move the imaging detectors 102 with respect to the subject 110, for example, individually, in segments or subsets, or simultaneously in a fixed relationship to one another. For example, in some embodiments, the gantry motor controller 132 may cause the imaging detectors 102 and/or one or more of the support members 112 to rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and right-left directions, for example. As a specific example, a large region of interest of the subject 110 (e.g., metastasis) may be imaged with relatively few imaging detectors 102 by moving the patient table 120 through an area of the gantry 104 having the imaging detectors 102 such that the same imaging detectors 102 may perform a scan of the entire region of interest.

The detector controller 136 may control movement of each of the imaging detectors 102 to move closer to and farther from a surface of the subject 110, such as by controlling translating movement of the detector carriers 116 linearly toward or away from the subject 110 (e.g., sliding or telescoping movement). Optionally, the detector controller 136 may control movement of the detector carriers 116 to allow coordinated movement of the detector array 106. The pivot controller 138 may control pivoting, rotating, or swinging movement of the detector units 114a, 114b at, or within, ends of the detector carriers 116. For example, one or more of the detector units 114a, 114b or detector carriers 116 may be pivoted or swung about at least one axis to view the subject 110 from a plurality of angular orientations. The collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller" may be used to indicate a collective name for all motion controllers (e.g., controllers 132, 136, 138). It should be noted that the various controllers may be combined, for example, the detector controller 136 and pivot controller 138 may be combined to provide the different movements described herein.

Prior to acquiring an image of the subject 110 or a portion of the subject 110, the imaging detectors 102, gantry 104, patient table 120, and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data. Positioning may be accomplished manually by the operator and/or automatically, which may include using other images acquired before the current acquisition, such as by another imaging modality such as computed tomography (CT), magnetic resonance imaging (MRI), x-ray, positron emission tomography (PET), or ultrasound. Additionally, the detector units 114a, 114b may be configured to acquire non-NM data, such as x-ray CT data.

After the imaging detectors 102, gantry 104, patient table 120, and/or collimators 122 are positioned, one or more images may be acquired by one or more of the imaging detectors 102 being used, which may include pivoting or swinging motion of one or more of the detector units 114a, 114b, which may pivot, rotate, or swing to different degrees or between different ranges of angles. The image data acquired by each imaging detector 102 may be combined and reconstructed into a composite image, which may include two-dimensional (2D) images, a three-dimensional (3D) volume, or a 3D volume over time, e.g., four dimensions (4D).

In one embodiment, the imaging detectors 102, gantry 104, patient table 120, and/or collimators 122 may remain stationary after being initially positioned. In another embodiment, an effective FOV for one or more of the imaging detectors 102 may be increased by movement such as pivoting, rotating, or swinging one or more of the imaging detectors 102, rotating the detector array 106 with the gantry 104, adjusting one or more of the collimators 122, or moving the patient table 120.

In various embodiments, a data acquisition system (DAS) 160 may receive electrical signal data produced by the imaging detectors 102 and converts the electrical signal data into digital signals for subsequent processing. An image reconstruction device 162 and a data storage device 164 may be provided in addition to the processing unit 150. It should be noted that one or more functions related to one or more of data acquisition, motion control, data processing, and image reconstruction may be accomplished through hardware, software, and/or by shared processing resources, which may be located within or near the NM imaging system 100, or may be located remotely. Additionally, a user input device 166 may be provided to receive user inputs (e.g., control commands), as well as a display 168 for displaying images.

Additionally, a detector position controller 165 may also be provided, which may be implemented in hardware, software, or a combination thereof. For example, as shown in FIG. 1, the detector position controller 165 may form part of, or operate in connection with, the processing unit 150. In some embodiments, the detector position controller 165 may be a module that operates to control the movement of the imaging detectors 102, including the detector units 114a, 114b, such that coordinated or synchronized movement is provided as described herein. It should be noted that movement of a plurality of the imaging detectors 102 and/or detector units 114a, 114b may be performed at the same time (e.g., simultaneously or concurrently) or at different times (e.g., sequentially or step-wise, such as back and forth between two detector units 114a and/or 114b). It also should be understood that when referring to a detector unit, such a detector unit may include one or multiple detector modules (e.g., CZT modules).

Figure 2A:
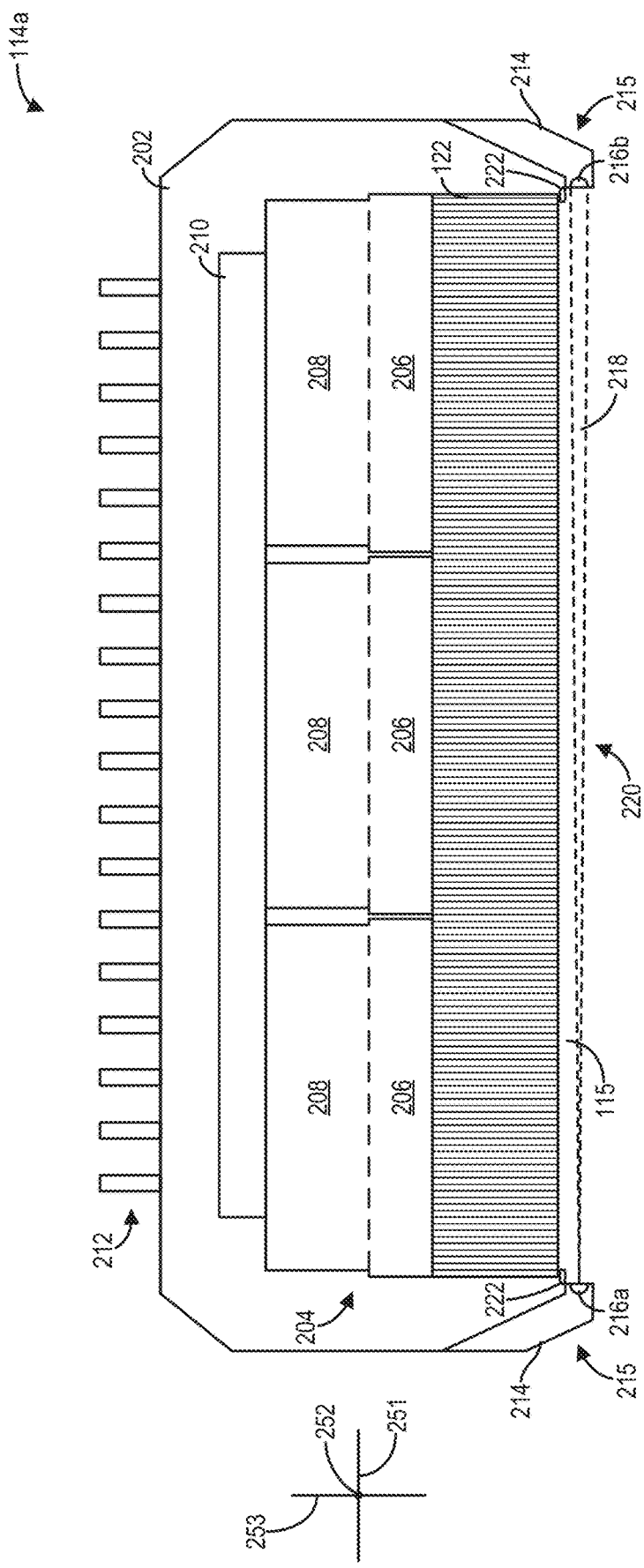
FIG. 2A shows a schematic diagram of a first detector unit for use in the NM imaging system, according to an embodiment.

Referring now to FIG. 2A, a cross-sectional view of the first detector unit 114a is depicted, showing three CZT modules 204, each indicative of a row of multiple CZT modules 204. It will be appreciated that in FIG. 2A, and in FIGS. 2B-3B (described in more detail below), mutually perpendicular axes 251, 252, and 253 define a three-dimensional space relative to the cross-sectional view, where the axis 251 and the axis 253 define a plane of the cross-sectional view and the axis 252 is normal to the plane of the cross-sectional view. Herein, the mutually perpendicular axes 251, 252, and 253 may be employed to describe an overall movement of the first detector unit 114a, as well as relative positioning of components of the first detector unit 114a with respect to one another. For example, each of the three rows of CZT modules 204 may be respectively aligned with the depicted CZT modules 204 and may extend along the axis 252, such that one or more CZT modules 204 may be in front of the plane of the cross-sectional view and one and/or one or more CZT modules 204 may be behind the plane of the cross-sectional view.

The first detector unit 114a may include a casing 202 which may house one or more of the various components of the first detector unit 114a, where the casing 202 may be a frame or other support structure. The casing 202 may be made of a high-density material, such as lead or tungsten, for example. The collimator 122 may be disposed within the casing 202. In specific embodiments wherein the collimator 122 is exchangeable, the collimator 122 may be removably fixed in place by a pair of adjustable locking mechanisms 222 such that the collimator 122 may be attached and detached upon application of pressure to each of the pair of adjustable locking mechanisms 222. The collimator 122 may include a plurality of septa, which may be configured to receive and narrow incoming radiation (e.g., gamma rays) for the CZT modules 204. The incoming radiation may be passed to CZT detector plates 206 respectively situated in the CZT modules 204. Each of the CZT modules 204 may further include electronics 208 (e.g., output electronics to output detected events) conductively coupling the CZT detector plate 206 to a printed circuit board (PCB) 210, such that NM imaging data may be acquired based on the incoming radiation. The NM imaging data may then be passed to the controller unit (e.g., 130) and the processing unit (e.g., 150) of the NM imaging system (e.g., 100), as described above with reference to FIG. 1. A heat sink (e.g., air or water cooling) 212 with a fan (not shown) may be disposed on, or positioned within, the casing 202, so as to prevent overheating of the various components therein during operation of the first detector unit 114a.

The first detector unit 114a may include a pair of proximity detectors 215 actuatable by optical feedback such that contact with the subject (e.g., 110) by the first detector unit 114a may be mitigated or avoided. As shown, the pair of proximity detectors 215 may be disposed opposite to one another, such that each of the pair of proximity detectors 215 reflects an opposite proximity detector 215 across a plane parallel to a plane including the axes 252 and 253. It will be appreciated that the pair of proximity detectors 215 may include any type of proximity sensor known in the art, such as further pressure sensors, optical sensors, capacitive sensors, and/or ultrasound sensors, within the scope of the present disclosure. For example, and as depicted at FIG. 2A, the pair of proximity detectors 215 may respectively include a pair of optical sensors 216a, 216b. The optical sensor 216a may be operable to project an LED beam 218 along the axis 251 and across a cavity 220 formed by the proximity detectors 215 extending from the surface 115 along the axis 253. Assuming no obstructing or obscuring object enters the cavity 220, the LED beam 218 may correspondingly be received by the optical sensor 216b. However, in some examples, an interfering object (e.g., a portion of the subject) may indeed enter the cavity 220. In such examples, the LED beam 218 may be interrupted and thereby prevented from reaching the optical sensor 216b. As such, appropriate movement of the first detector unit 114a may be automatically actuated so that the interfering object and/or the first detector unit 114a is not subjected to undue pressure (e.g., the first detector unit 114a may translate along the axis 253 away from the interfering object, as described in detail with reference to FIGS. 5A-5C below).

Each of the pair of proximity detectors 215 may additionally or alternatively include a sliding-end contact sensor 214. The sliding-end contact sensors 214 may be actuated (e.g., depressed along the axis 253) by a threshold pressure applied thereto by an interfering object (e.g., a portion of the subject, e.g., 110, or another detector unit 114a, 114b). Thus, and as described in detail below with reference to FIGS. 6A-6C, when the interfering object actuates at least one of the sliding-end contact sensors 214, the LED beam 218 may be interrupted and therefore may not reach the optical sensor 216b. As such, appropriate movement of the first detector unit 114a may be automatically actuated so that the interfering object and/or the first detector unit 114a is not subjected to undue pressure (e.g., the first detector unit 114a may pivot away from the interfering object around an axis parallel to the axis 252).

Figure 2B:
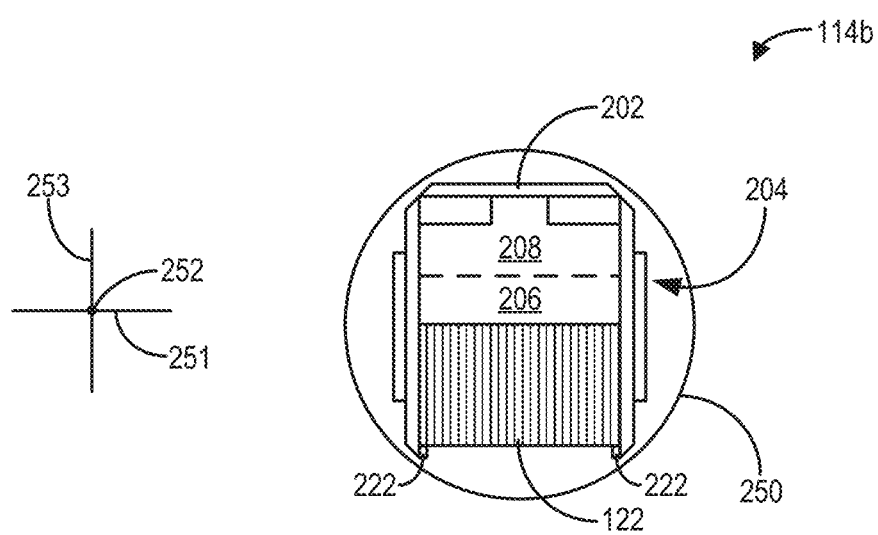
FIG. 2B shows a schematic diagram of a second detector unit for use in the NM imaging system, according to an embodiment.

Referring now to FIG. 2B, a cross-sectional view of the second detector unit 114b is depicted, showing one CZT module 204, which may be indicative of a row of multiple CZT modules 204. Herein, the mutually perpendicular axes 251, 252, and 253 may be employed to describe an overall movement of the second detector unit 114b, as well as relative positioning of components of the second detector unit 114b with respect to one another. For example, the row of CZT modules 204 may be respectively aligned with the depicted CZT module 204 and may extend along the axis 252, such that one or more CZT modules 204 may be in front of the plane of the cross-sectional view and one and/or one or more CZT modules 204 may be behind the plane of the cross-sectional view.

As can be seen in the illustrated embodiment, the second detector unit 114b may include a housing 250, which is depicted as circular. However, the housing 250 may be configured in different shapes and sizes, for example, oval, other curved shapes, etc. The second detector unit 114b may include the casing 202 within the housing 250, where the casing 202 may be a frame or other support structure. The casing 202 may be made of a high-density material, such as lead or tungsten, for example. Further, the CZT module 204 may be coupled to the casing 202 via the CZT detector plate 206 included therein. The CZT module 204 may further include electronics 208 (e.g., output electronics to output detected events) conductively coupled to the CZT detector plate 206, such that NM imaging data may be acquired based on the incoming radiation. In additional or alternative embodiments, a PCB (e.g., 210; not shown) may further be conductively coupled to the electronics 208 for receiving and passing the NM imaging data. Additionally, the collimator 122 may be mounted to a front detecting surface of the CZT detector plate 206. In specific embodiments wherein the collimator 122 is exchangeable, the collimator 122 may be removably fixed in place by a pair of adjustable locking mechanisms 222 such that the collimator 122 may be attached and detached upon application of pressure to each of the pair of adjustable locking mechanisms 222. The collimator 122 may include a plurality of septa, which may be configured to receive and narrow incoming radiation (e.g., gamma rays) for the CZT modules 204. Thus, the casing 202 may be sized and shaped, such as having a base and/or walls, to support and maintain various components of the second detector unit 114b within the housing 250. For example, the components of the second detector unit 114b may be maintained within the housing 250 when the housing rotates, pivots, or swings. It should be noted that in some embodiments, the housing 250 may not be provided to surround or encase the components within the second detector unit 114b.

As seen in FIG. 2B, the housing 250 for the second detector unit 114b may generally be circular in shape. As such, pivoting of a given second detector unit 114b about a center thereof (as described below with reference to FIG. 3B) may not physically interfere with adjacent detector units (e.g., 114a, 114b). The housing 250 may thus allow for a small clearance in between each detector unit 114a, 114b to allow for maximal pivoting motion of each second detector unit 114b during operation of the NM imaging system 100.

Returning now to FIG. 2A, the first detector unit 114a provided by an embodiment of the present disclosure may be optimized for flexible, high-resolution NM imaging. As a first example, no obstructing external housing (e.g., 250) may be disposed around the first detector unit 114a, permitting the first detector unit 114a to be moved as close as possible to the subject (e.g., 110) to be imaged. Indeed, the proximity detectors 215 may preclude use of such external housings, as the proximity detectors 215 may mitigate discomfort to the subject by automatically adjusting the first detector unit 114a near to, but not in contact with, the subject upon actuation of at least one of the proximity detectors 215. In contrast, the second detector unit 114b may not possess such features. However, a smaller overall size of the second detector unit 114b may allow smaller subjects to be imaged with less interference from adjacent detector units 114a, 114b. As a second example, the multiple rows of CZT modules 204 may provide proportionally greater imaging resolution to the first detector unit 114a as compared to the second detector unit 114b (which may include a single row of CZT modules), as the multiple rows of CZT modules 204 may provide increased image sampling. Thus, in the depicted example, the first detector unit 114a, having three rows of CZT modules 204, may correspondingly have three times the imaging resolution of the second detector unit 114b. As a third example, and as described in detail below with reference to FIG. 3A, the first detector unit 114a may be configured to move along multiple degrees of freedom. It will be appreciated that the second detector unit 114b may move along multiple degrees of freedom in a similar fashion, as described in detail below with reference to FIG. 3B. Such movement may correspondingly facilitate conformation of the detector units 114a, 114b, and thus the entire detector array (e.g., 106), to the subject. In this way, an amount of "dead shielding" space (e.g., imaged space not corresponding to the subject) may be reduced.

Referring now to FIGS. 3A and 3B, schematic diagrams 300 and 350 of the imaging detector 102 respectively including the first detector unit 114a and the second detector unit 114b are depicted. The imaging detector 102 may additionally include the detector carrier 116. Further respectively shown are a number of degrees of freedom of the first detector unit 114a and the second detector unit 114b which may be actuated by various mechanical components of the NM imaging system (e.g., 100) and controlled by the controller unit (e.g., 130) thereof. For example, the imaging detector 102 may be affixed to the gantry 104, or support members thereof (e.g., 112), such as a track 304. In some embodiments, the track 304 may circumscribe an inner surface 306 of the gantry 104, where the imaging detector 102 may be positioned partially within the track 304. Specifically, in some examples, the track 304 may be an open space through which the detector carrier 116 may extend from an internal rotational mechanism. In other examples, a support mechanism to facilitate movement, such as wheels, may be placed within the track and coupled to the detector carrier 116. As such, the imaging detector 102 may move with the gantry 104 or may move independently from the gantry 104 along the track 304. Further, the imaging detector 102 may extend within the aperture (e.g., 118; not shown at FIGS. 3A and 3B) of the gantry 104. Specifically, the imaging detector 102 may extend orthogonally toward a rotational axis 308 located at a center of the gantry 104 and tracing a length of the aperture thereof. As shown in the schematic diagram 300, carried by the detector carrier 116, the first detector unit 114a may therefore rotate 302 around the rotational axis 308 (not shown to scale). The rotational axis 308 may be parallel to the axis 252. It will be appreciated that, in embodiments wherein the gantry 104 is configured in an annular shape (as depicted in FIG. 1), the first detector unit 114a may fully, or completely, rotate 302 around the rotational axis 308. However, in other examples, any given first detector unit 114a in the detector array (e.g., 106) may have limited rotation 302 about the rotational axis 308, such as up to 180°, 90°, 60°, etc. Similarly, as shown in the schematic diagram 350, carried by the detector carrier 116, the second detector unit 114b may therefore rotate 352 around the rotational axis 308 (not shown to scale). The rotational axis 308 may be parallel to the axis 252. It will be appreciated that, in embodiments wherein the gantry 104 is configured in an annular shape (as depicted in FIG. 1), the second detector unit 114b may fully, or completely, rotate 352 around the rotational axis 308. However, in other examples, any given second detector unit 114b in the detector array (e.g., 106) may have limited rotation 352 about the rotational axis 308, such as up to 180°, 90°, 60°, etc.

As another example, the detector carrier 116 may include a plurality of telescoping segments (e.g., 314a, 314b, 314c). The plurality of telescoping segments may collapse into one another toward the gantry 104 along the axis 253. For example, the telescoping segment 314a may collapse into the telescoping segment 314b and the telescoping segment 314b may collapse into the telescoping segment 314c, such that the plurality of telescoping segments may be in a fully collapsed, or retracted, position. The schematic diagrams 300 and 350, however, depict the plurality of telescoping segments in a fully extended position. In this way, and as shown in the schematic diagram 300, the first detector unit 114a may translate 312 along the axis 253 within physical limitations of the detector carrier 116 (e.g., the detector carrier 116 may be in any position between the fully collapsed position and the fully extended position). Similarly, and as shown in the schematic diagram 350, the second detector unit 114b may translate 362 along the axis 253 within physical limitations of the detector carrier 116 (e.g., the detector carrier 116 may be in any position between the fully collapsed position and the fully extended position).

As yet another example, as shown in the schematic diagram 300, the first detector unit 114a may be configured to pivot 322 independently from the detector carrier 116. That is, while the first detector unit 114a may remain affixed to the detector carrier 116, the first detector unit 114a may pivot 322 around a pivoting axis 324 located at a center thereof. As shown, the pivoting axis 324 may be parallel to each of the axis 252 and the rotational axis 308. It will be appreciated that the first detector unit 114a may not pivot completely around the pivoting axis 324, as mechanical restrictions may preclude complete pivoting. However, the first detector unit 114a may move within a limited range from a default configuration, such as the configuration depicted in schematic diagram 300. In some embodiments, the first detector unit 114a may pivot 322 up to 60° from the default configuration. In additional or alternative embodiments, the first detector unit 114a may pivot 322 up to 30° from the default configuration. In additional or alternative embodiments, the first detector unit 114a may pivot 322 up to 20° from the default configuration. In additional or alternative embodiments, the first detector unit 114a may pivot 322 up to 15° from the default configuration. In additional or alternative embodiments, the first detector unit 114a may pivot 322 up to 10° from the default configuration.

Similarly, as shown in the schematic diagram 350, the second detector unit 114b may be configured to pivot 372 independently from the detector carrier 116. That is, while the second detector unit 114b may remain affixed to the detector carrier 116, the second detector unit 114b may pivot 372 around a pivoting axis 374 located at a center thereof. As shown, the pivoting axis 374 may be parallel to each of the axis 252 and the rotational axis 308. It will be appreciated that the second detector unit 114b may not pivot completely around the pivoting axis 374, as mechanical restrictions may preclude complete pivoting. However, the second detector unit 114b may move within a limited range from a default configuration, such as the configuration depicted in schematic diagram 350. In some embodiments, the second detector unit 114b may pivot 372 up to 90° from the default configuration. In some embodiments, the second detector unit 114b may pivot 372 up to 60° from the default configuration. In additional or alternative embodiments, the second detector unit 114b may pivot 372 up to 30° from the default configuration. In additional or alternative embodiments, the second detector unit 114b may pivot 372 up to 20° from the default configuration. In additional or alternative embodiments, the second detector unit 114b may pivot 372 up to 15° from the default configuration. In additional or alternative embodiments, the second detector unit 114b may pivot 372 up to 10° from the default configuration. In some embodiments, the second detector unit 114b may have greater freedom of movement around the pivoting axis 374 than the first detector unit 114a has around the pivoting axis 324.

In this way, the detector units 114a, 114b may at least move about one rotational axis, one translational axis, and one pivoting axis, such that the detector array (e.g., 106) including a plurality of detector units 114a, 114b may be operable to conform to a subject to be imaged. It will be appreciated that other movements of the detector units 114a, 114b may be contemplated and implemented by one of ordinary skill in the art, and that the present disclosure is not to be interpreted as limited to the degrees of freedom described with reference to FIGS. 3A and 3B.

Referring now to FIGS. 4A and 4B, schematic diagrams 400 and 425 are depicted, illustrating an exemplary process for conforming the detector array 106 to a subject 410 (represented in FIGS. 4A and 4B as a cross-sectional slice thereof). As described above with reference to FIG. 1, the detector array 106 may include a plurality of imaging detectors 102, each imaging detector 102 including the detector carrier 116 and one of the first detector unit 114a and the second detector unit 114b. Further, the detector array 106 may be formed within the aperture 118 of the gantry 104, whereby the detector array 106 may be directly coupled to the gantry 104 or to the support members 112 thereof.

As shown in the schematic diagram 400, the plurality of detector units 114a, 114b may be configured in a number of initial positions, which may not be optimal for imaging of the subject 410. That is, at least some of the collimators 122 of the plurality of detector units 114a, 114b may be oriented in a direction at least partially facing away from the subject 410. Further, the plurality of detector units 114a, 114b may be retracted away from the subject 410 to allow the subject 410 to freely enter the aperture 118, which may further preclude optimal imaging resolution.

In examples wherein a size of the subject to be imaged is large, each of the first detector units 114a may move independently to conform to the subject 410. For example, automatic body contouring may be implemented by the NM imaging system (e.g., 100), which may provide an estimated outer perimeter of the subject 410. Based on respective positions thereof, each of the first detector units 114a may therefore move to align toward the estimated outer perimeter. In the schematic diagram 400, for example, one of the first detector units 114a is shown as translating 402 toward the subject 410. The one of the first detector units 114a is further shown as pivoting 404 so as to align the collimator 122 thereof for optimal receipt of incoming radiation from the subject 410. Each remaining first detector unit 114a may similarly adjust a position thereof to acquire NM imaging data of an increased imaging resolution. Further, each of the second detector units 114b, interposed between the first detector units 114b in the schematic diagram 400, may also move to align toward the estimated outer perimeter to provide further imaging resolution.

As such, the plurality of detector units 114a, 114b may move to a final position, as depicted in the schematic diagram 425. In this way, the detector array 106 may be optimized for subjects of varying sizes and shapes, providing an NM imaging system with high imaging flexibility. As shown, the final position of the detector units 114a, 114b may be adjacent to, but not in contact with, the subject 410.

In some embodiments, automatic body contouring alone may not be sufficient to prevent the plurality of first detector units 114a from contacting the subject 410. For example, automatic body contouring may estimate an outer perimeter of the subject 410 which, at least in part, may lie within an actual perimeter of the subject 410. Thus, when a given first detector unit 114a attempts to conform to the outer perimeter estimated by the automatic body contouring, the given first detector unit 114a may contact the subject 410. Such contact may be mitigated via proximity detectors (e.g., 215) included in each first detector unit 114a, where the proximity detectors may include optical sensors (e.g., 216a, 216b) and sliding-end contact sensors (e.g., 214) for providing feedback regarding positioning of the first detector units 114a relative to an actual location of the subject 410 (that is, not based on the estimated outer perimeter alone). However, since the second detector units 114b may not include proximity detectors similar to those of the first detector units 114a, the second detector units 114b may remain further from the estimated outer perimeter than the first detector units 114a, thereby mitigating contact with the subject 410.

Referring now to FIGS. 4C and 4D, schematic diagrams 450 and 475 are depicted, illustrating an exemplary process for conforming the detector array 106 to a subject 460 (represented in FIGS. 4C and 4D as a cross-sectional slice thereof). As described above with reference to FIG. 1, the detector array 106 may include a plurality of imaging detectors 102, each imaging detector 102 including the detector carrier 116 and one of the first detector unit 114a and the second detector unit 114b. Further, the detector array 106 may be formed within the aperture 118 of the gantry 104, whereby the detector array 106 may be directly coupled to the gantry 104 or to the support members 112 thereof.

As shown in the schematic diagram 450, the plurality of detector units 114a, 114b may be configured in a number of initial positions, which may not be optimal for imaging of the subject 460. That is, at some of the collimators 122 of the plurality of detector units 114a, 114b may be oriented in a direction at least partially facing away from the subject 460. Further, the plurality of detector units 114a, 114b may be retracted away from the subject 410 to allow the subject 410 to freely enter the aperture 118, which may further preclude optimal imaging resolution.

In examples wherein a size of the subject to be imaged is small, such as the subject 460, the first detector units 114a, having a larger size than the second detector units 114b, may remain retracted so as not to obstruct one another upon imaging. With the first detector units 114a retracted, each of the second detector units 114b may move independently to conform to the subject 460. For example, automatic body contouring may be implemented by the NM imaging system (e.g., 100), which may provide an estimated outer perimeter of the subject 460. Based on respective positions thereof, each of the second detector units 114b may therefore move to align toward the estimated outer perimeter. In the schematic diagram 450, for example, one of the second detector units 114b is shown as translating 452 toward the subject 460. The one of the first detector units 114b is further shown as pivoting 454 so as to align the collimator 122 thereof for optimal receipt of incoming radiation from the subject 460. Each remaining second detector unit 114b may similarly adjust a position thereof to acquire NM imaging data of an increased imaging resolution.

As such, the plurality of detector units 114a, 114b may move to a final position, as depicted in the schematic diagram 475. In this way, the detector array 106 may be optimized for subjects of varying sizes and shapes, providing an NM imaging system with high imaging flexibility. As shown, while the first detector units 114a remain retracted, the final position of the second detector units 114b may be adjacent to, but not in contact with, the subject 460. Indeed, since the second detector units 114b may not include proximity detectors similar to those of the first detector units 114a, the second detector units 114b may remain further from the estimated outer perimeter than would the first detector units 114a conforming to an estimated outer perimeter of a given subject, thereby mitigating contact with the subject 460.

It will be appreciated that the processes depicted by FIGS. 4A-4D are merely exemplary, and that examples may be contemplated within the scope of the present disclosure in which each of the first detector units 114a and the second detector units 114b are used in imaging of a subject (e.g., a subject having an irregular size, where only some of the first detector units 114a may remain reracted).

Referring now to FIGS. 5A-5C, schematic diagrams 500, 520, 540 are depicted, illustrating an exemplary process for adjusting a position of the imaging detector 102 when the first detector unit 114a thereof moves near a subject 502 via extension of the detector carrier 116. The first detector unit 114a may include the pair of proximity detectors 215, where the pair of proximity detectors 215 may respectively include one of the optical sensors 216a, 216b. As such, feedback from the proximity detectors 215 may be utilized by the controller unit (e.g., 130) described above with reference to FIG. 1 to determine a proximity of the first detector unit 114a to the subject 502. It will be appreciated that the subject 502 is depicted in the schematic diagrams 500, 520, 540 as a portion thereof, and that the subject 502 may extend beyond the dashed line 504.

As shown in the schematic diagram 500, the detector carrier 116 may extend in a direction 506, translating the first detector unit 114a toward the subject 502. As described in detail above with reference to FIG. 3, the detector carrier 116 may include the plurality of telescoping segments (not shown at FIGS. 5A-5C), enabling such extension of the detector carrier 116. As further shown, the optical sensor 216a may project the LED beam 218, which may be correspondingly received by the optical sensor 216b.

After extension of the detector carrier 116, the first detector unit 114a may be positioned as shown in the schematic diagram 520. As shown, a portion of the subject 502 may obstruct 522 the LED beam 218 from reaching the optical sensor 216b. As such, feedback from the optical sensor 216b, or lack thereof, may indicate that the first detector unit 114a has been positioned too close to, but may not be contacting, the subject 502.

As such, and as shown in the schematic diagram 540, the detector carrier 116 may retract in the direction 542, translating the first detector unit 114a away from the subject 502. In some examples, the detector carrier 116 may be configured to retract to just beyond a predetermined distance from where the obstruction 522 occurred. In other examples, the detector carrier 116 may be configured to retract until the LED beam 218 is again received by the optical sensor 216b. As such, a high imaging resolution may be retained by maintaining the proximity of the first detector unit 114a to the subject 502. In this way, in some examples, the first detector unit 114a may automatically avoid contacting the subject 502, thereby mitigating excess pressure to the various components of the first detector unit 114a and discomfort to the subject 502.

Referring now to FIGS. 6A-6C, schematic diagrams 600, 620, 640 are depicted, illustrating an exemplary process for adjusting a position of the imaging detector 102 when the first detector unit 114a thereof moves near a subject 602 via extension of the detector carrier 116 or pivoting of the first detector unit 114a thereon. The first detector unit 114a may include the pair of proximity detectors 215, where the pair of proximity detectors 215 may respectively include one sliding-end contact sensor 214 and one of the optical sensors 216a, 216b. As such, feedback from the proximity detectors 215 may be utilized by the controller unit (e.g., 130) described above with reference to FIG. 1 to determine a proximity of the first detector unit 114a to the subject 602. It will be appreciated that the subject 602 is depicted in the schematic diagrams 600, 620, 640 as a portion thereof, and that the subject 602 may extend beyond the dashed line 604.

As shown in the schematic diagram 600, the detector carrier 116 may extend in a direction 606, translating the first detector unit 114a toward the subject 602. As described in detail above with reference to FIGS. 3A and 3B, the detector carrier 116 may include the plurality of telescoping segments (not shown at FIGS. 6A-6C), enabling such extension of the detector carrier 116. In some examples, the first detector unit 114a may additionally pivot toward the subject 602. As further shown, the optical sensor 216a may projected the LED beam 218, which may be correspondingly received by the optical sensor 216b.

After extension of the detector carrier 116 and/or pivoting of the first detector unit 114a, the first detector unit 114a may be positioned as shown in the schematic diagram 620. As shown, the first detector unit 114a may contact 622 the subject 602, thereby actuating (e.g., depressing) one of the sliding-end contact sensors 214. Once actuated, the sliding-end contact sensor 214, being mechanically coupled to the optical sensor 216b, may move the optical sensor 216b out of a path of the LED beam 218. As such, feedback from the optical sensor 216b, or lack thereof, may indicate that the first detector unit 114a has pivoted such that a corner thereof including one of the pair of proximity detectors 215 has contacted the subject 602.

As such, and as shown in the schematic diagram 640, the first detector unit 114a may pivot in the direction 642, moving the first detector unit 114a away from the subject 602. The first detector unit 114a may be configured to pivot until the actuated sliding-end contact sensor 214 returns to a default position (e.g., the position depicted by the schematic diagrams 600, 640), such that a high imaging resolution may be retained by maintaining the proximity of the first detector unit 114a to the subject 602. In this way, in some examples, the first detector unit 114a may automatically pivot away from the subject 602 upon actuation of the sliding-end contact sensor 214 under light pressure, thereby mitigating excess pressure on the various components of the first detector unit 114a and discomfort to the subject 602. It will further be appreciated that, though the pair of sliding-end contact sensors 214 are coupled with the pair of optical sensors 216a, 216b in the exemplary process depicted by FIGS. 6A-6C, that the exemplary process may be executed based on the pressure feedback received by at least one of the pair of sliding-end contact sensors 214 absent the pair of optical sensors 216a, 216b.

Referring now to FIGS. 7A-7D, schematic diagrams 700, 725, 750, 775 are depicted, showing various exemplary configurations of the gantry 104 and the detector array 106. The detector array 106 may either be affixed to the gantry 104 or to the support members 112 thereof. As shown, the detector array 106 may include the plurality of imaging detectors 102, each of the plurality of imaging detectors 102 respectively including one of the first detector unit 114a and the second detector unit 114b positioned on the detector carrier 116. Each of the detector units 114a, 114b may respectively include the collimator 122 for receiving and focusing incoming radiation from a subject (not shown at FIGS. 7A-7D). In the exemplary configurations of FIGS. 7A-7D, the gantry 104 is configured as a substantially circular ring having the cylindrical aperture 118 therethrough. It will be appreciated, however, that the exemplary configurations of FIGS. 7A-7D are not to be interpreted as limiting the present disclosure, and that any configuration of the detector array 106 and the gantry 104 may be contemplated and implemented by one of ordinary skill in the art.

As a first example, and as shown in the schematic diagram 700, the detector array 106 may include six imaging detectors 102 positioned in a default configuration (e.g., prior to movements of individual imaging detectors 102) on the gantry 104, wherein three of the six imaging detectors 102 respectively including the first detector unit 114a are spaced approximately 120° from one another and a remaining three of the six imaging detectors 102 respectively including the second detector unit 114b are spaced approximately 120° from one another, interposed between the three imaging detectors having the first detector units 114a. As a second example, and as shown in the schematic diagram 725, the detector array 106 may include nine imaging detectors 102 positioned in a default configuration (e.g., prior to movements of individual imaging detectors 102) on the gantry 104, wherein three of the nine imaging detectors 102 respectively including the first detector unit 114a are spaced approximately 120° from one another and a remaining six of the nine imaging detectors 102 respectively including the second detector unit 114b are interposed in pairs between the three imaging detectors having the first detector units 114a. As a third example, and as shown in the schematic diagram 750, the detector array 106 may include nine imaging detectors 102 positioned in a default configuration (e.g., prior to movements of individual imaging detectors 102) on the gantry 104, wherein three of the nine imaging detectors 102 respectively including the second detector unit 114b are spaced approximately 120° from one another and a remaining six of the nine imaging detectors 102 respectively including the first detector unit 114a are interposed in pairs between the three imaging detectors having the second detector units 114b. As a fourth example, and as shown in the schematic diagram 775, the detector array 106 may include twelve imaging detectors 102 positioned in a default configuration (e.g., prior to movements of individual imaging detectors 102) on the gantry 104, wherein six of the twelve imaging detectors 102 respectively including the first detector unit 114a are spaced approximately 60° from one another and a remaining six of the twelve imaging detectors 102 respectively including the second detector unit 114b are spaced approximately 60° from one another, interposed between the six imaging detectors having the first detector units 114a.

Figure 8:
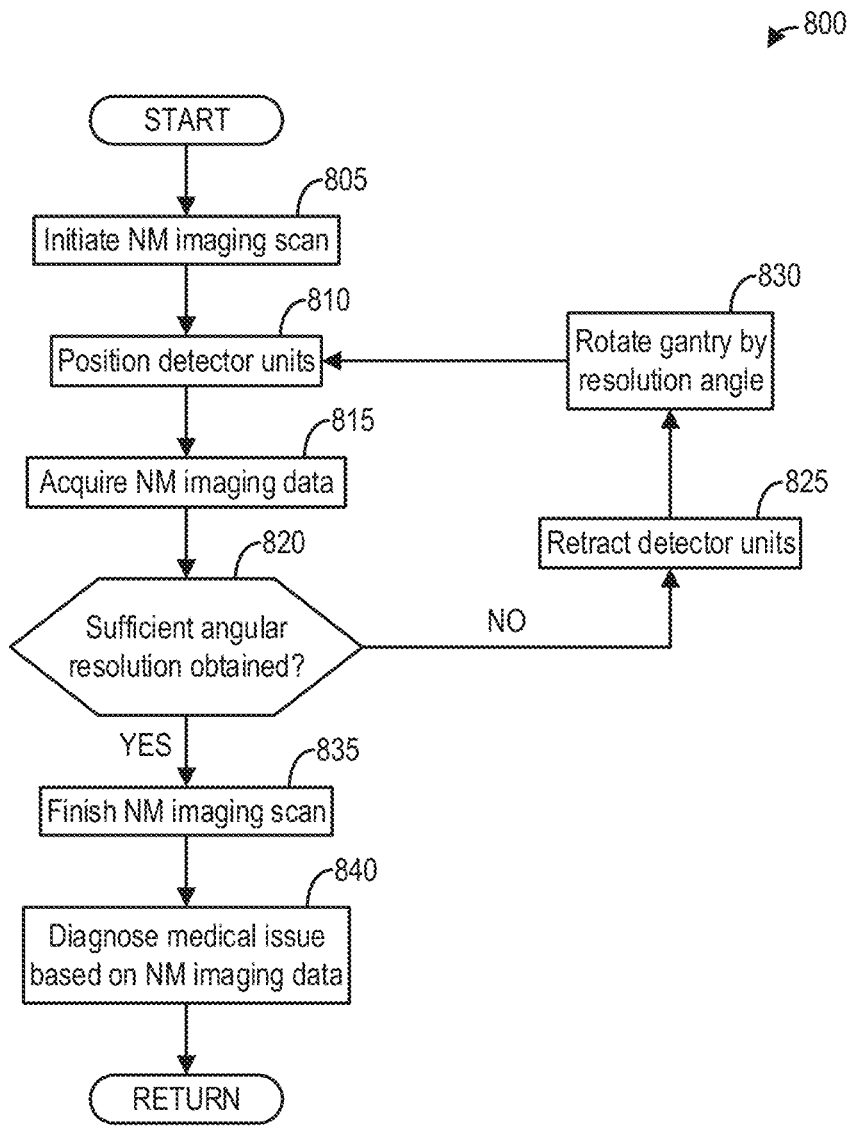
FIG. 8 shows a flow chart of a method for imaging a subject via the NM imaging system, according to an embodiment.

Referring now to FIG. 8, a flow chart is depicted, showing a method 800 for imaging a subject via an NM imaging system. Execution of the method 800 may depend upon various degrees of freedom via which detector units of the NM imaging system may move, such that the detector units are positioned to optimally image a subject.

Method 800 is described below with regard to the systems and components depicted in FIGS. 1 and 2, though it should be appreciated that method 800 may be implemented with other systems and components without departing from the scope of the present disclosure. In some embodiments, method 800 may be implemented as executable instructions in any appropriate combination of the NM imaging system 100, an edge device (e.g., an external computing device) connected to the NM imaging system 100, a cloud in communication with the NM imaging system 100, and so on. As one example, method 800 may be implemented in non-transitory memory of a computing device, such as the processing unit 150 of the NM imaging system 100 in FIG. 1 (e.g., in communication with the controller unit 130 of the NM imaging system 100).

Method 800 may begin at 805, where an NM imaging scan may be initiated. The NM imaging scan may include receiving incoming radiation from the subject (e.g., 110) at the detector units (e.g., 114a, 114b). However, each of the detector units may not yet be positioned for optimal imaging by the NM imaging system (e.g., 100), and therefore, at 810, method 800 may include positioning the detector units prior to actively acquiring NM imaging data at 815. Positioning the detector units may include translating and/or pivoting the detector units via various degrees of freedom such that the detector units may be positioned adjacent to, but not in contact with, the subject. In this way, the detector units may be coordinated to move to a first position to receive the incoming radiation from the subject.

Once the detector units (e.g., 114a, 114b) are positioned, the incoming radiation may pass through, and be narrowed by, the collimators (e.g., 122) associated with the various detector units. The incoming radiation may be passed to respective CZT modules (e.g., 204), such that, at 815, the NM imaging data may be acquired.

At 820, method 800 may include determining whether sufficient angular resolution of the NM imaging data has been obtained by the detector array (e.g., 106). In some embodiments, the detector array may be rotated via the gantry (e.g., 104) such that individual imaging detectors (e.g., 102) do not superimpose a prior angular position of any other imaging detector. For example, if the imaging detectors are disposed every 60° around a circular gantry, then the gantry may rotate by less than 60° (referred to herein as a resolution angle) and the subject (e.g., 110) may be reimaged to obtain further angular resolution.

Specifically, if sufficient angular resolution has not been obtained by the detector array (e.g., 106), method 800 may proceed to 825 to retract the detector units (e.g., 114a, 114b) via the detector carriers (e.g., 116). In some embodiments, retracting the detector units via the detector carriers may include collapsing a plurality of telescoping segments of the detector carriers to a fully collapsed position. Once the detector units are retracted, method 800 may include, at 830, rotating the gantry (e.g., 104) by the resolution angle. Method 800 may then return to 810 to again position the detector units for imaging. In this way, the detector units may be coordinated to move to a second position to receive further incoming radiation from the subject.

If sufficient angular resolution has been obtained by the detector array (e.g., 106), method 800 may proceed to 835 to finish the NM imaging scan (e.g., no further NM imaging data may be acquired until another NM imaging scan is initiated). Then, at 840, method 800 may include diagnosing a medical issue based on the NM imaging data. Diagnosing the medical issue may be performed by a medical professional upon analysis of the NM imaging data acquired during the NM imaging scan. For example, an area within the subject (e.g., 110) may be afflicted by a medical issue. The area within the subject may be imaged during the NM imaging scan, and the NM imaging system (e.g., 100) provided by an embodiment of the present disclosure may generate more precise and consistent NM imaging data as compared to conventional NM imaging systems. In this way, an accuracy of the diagnosis of the medical issue may be improved and may be made more consistent between medical professionals. Method 800 may then end.

Figure 9:
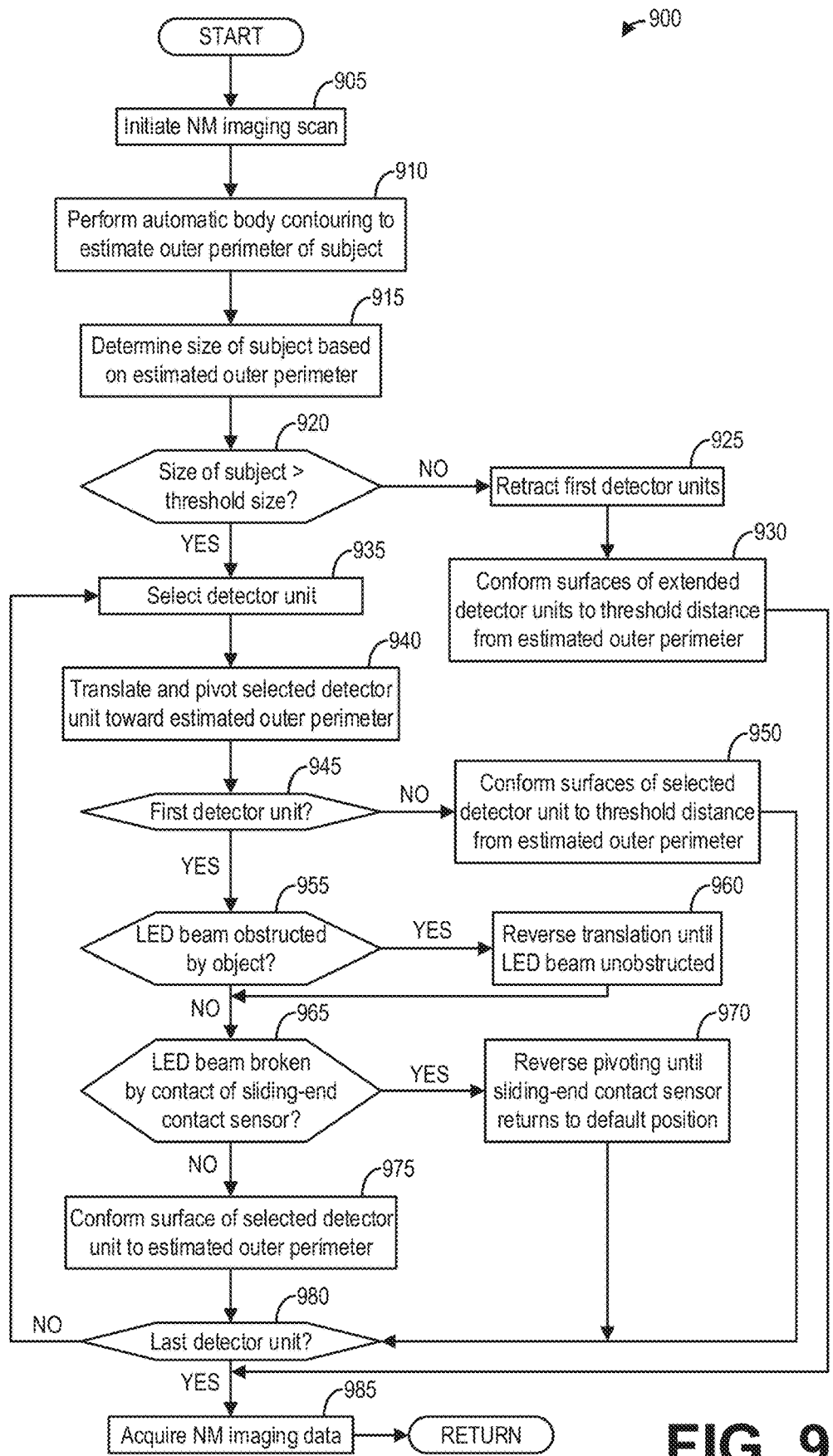
FIG. 9 shows a flow chart of a method for positioning the detector array of the NM imaging system to image a subject, according to an embodiment.

Referring now to FIG. 9, a flow chart is depicted, showing a method 900 for positioning a detector array of an NM imaging system to image a subject. Execution of the method 900 may depend upon various degrees of freedom via which detector units of the detector array may move, such that the detector units are positioned to optimally image a subject. As such, in some examples, method 900 may be used in place of 810 and 815 of method 800, whereby method 800 may continue at 820 following completion of method 900.

Method 900 is described below with regard to the systems and components depicted in FIGS. 1 and 2, though it should be appreciated that method 900 may be implemented with other systems and components without departing from the scope of the present disclosure. In some embodiments, method 900 may be implemented as executable instructions in any appropriate combination of the NM imaging system 100, an edge device (e.g., an external computing device) connected to the NM imaging system 100, a cloud in communication with the NM imaging system 100, and so on. As one example, method 900 may be implemented in non-transitory memory of a computing device, such as the processing unit 150 of the NM imaging system 100 in FIG. 1 (e.g., in communication with the controller unit 130 of the NM imaging system 100).

Method 900 may begin at 905, where an NM imaging scan may be initiated. The NM imaging scan may include receiving incoming radiation from the subject (e.g., 110) at the detector units (e.g., 114a, 114b). However, each of the detector units may not yet be positioned for optimal imaging by the NM imaging system (e.g., 100). As such, method 900, from 910 to 980, may include determining a final position for the detector units prior to actively acquiring NM imaging data at 985.

Such a determination of the final position for the detector units (e.g., 114a, 114b) may begin at 910, where method 900 may include performing an automatic body contouring routine to estimate an outer perimeter of the subject (e.g., 110). For example, sensors included in at least one detector unit may be operable to receive optical feedback based on external surfaces of the subject. As such, an approximate location of the subject and a volume thereof may be determined, such that the outer perimeter relative to a location of a given detector unit including the sensors may be estimated.

At 915, method 900 may include determining a size of the subject (e.g., 110) based on the estimated outer parameter. The size may include one of a total volume and a cross-sectional area adjacent to the detector units (e.g., 114a, 114b) operating in the NM imaging scan.

At 920, method 900 may include determining whether the size of the subject (e.g., 110) is greater than a threshold size. The threshold size may be a predetermined value based on a configuration of the detector array (e.g., 106) and sizes of the individual detector units (e.g., 114a, 114b).

For example, if the size of the subject (e.g., 110) is less than the threshold size, method 900 may proceed to 925 to retract the first detector units (e.g., 114a). Specifically, the first detector units may be larger than the second detector units (e.g., 114b). As such, the first detector units may obstruct one another when attempting to image a smaller subject, and may therefore remain retracted in such examples.

At 930, method 900 may include conforming the surfaces (e.g., 115) of the extended detector units (e.g., 114b) facing the subject (e.g., 110) to a threshold distance from the estimated outer perimeter. Specifically, since the first detector units (e.g., 114a) may be retracted for small subjects, only the second detector units may remain extended. However, the second detector units may not be equipped with the pair of proximity detectors (e.g., 215). As such, the threshold distance may be set to retain a small space between the second detector units and the subject, thereby reducing a likelihood of the second detector units contacting the subject. It will be appreciated that, though 930 is directed to simultaneous adjustment of positions of the various extended detector units in the detector array (e.g., 106), 930 may be executed sequentially for each given extended detector unit in the detector array (e.g., the extended detector units in the detector array may be positioned in a sequential order).

Once the surfaces (e.g., 115) of the extended detector units (e.g., 114b) have been conformed to the threshold distance from the estimated outer perimeter, the detector array (e.g., 106) may be considered in position for optimal imaging. Thus, during the NM imaging scan, the incoming radiation may pass through, and be narrowed by, the collimators (e.g., 122) associated with the various extended detector units. The incoming radiation may be passed to respective CZT modules (e.g., 204) such that, at 985, the NM imaging data may be acquired. Method 900 may then end.

Alternatively, if the size of the subject (e.g., 110) is greater than or equal to the threshold size, method 900 may proceed to 935 to select one of the detector units (e.g., 114a, 114b) of the detector array (e.g., 106). It will be appreciated that, though 935 to 980 are directed to sequential adjustment of positions of the various detector units in the detector array, 935 to 980 may be executed simultaneously for each given detector unit in the detector array (e.g., each of the detector units in the detector array may be positioned simultaneously to one another).

At 940, method 900 may include translating and pivoting the selected detector unit (e.g., 114a, 114b) toward the estimated outer perimeter. Translation and pivoting of the selected detector unit may include moving along various degrees of freedom (e.g., the various axes as described above with reference to FIG. 3) to closely approximate the estimated outer perimeter.

At 945, method 900 may include determining whether the selected detector unit is the larger, first detector unit (e.g., 114a) or the smaller, second detector unit (e.g., 114b). If the selected detector unit is the second detector unit, method 900 may proceed to 950 to conform the surfaces (e.g., 115) of the selected detector unit facing the subject (e.g., 110) to a threshold distance from the estimated outer perimeter. Specifically, since the second detector units may not be equipped with the pair of proximity detectors (e.g., 215), the threshold distance may be set to retain a small space between the selected second detector unit and the subject, thereby reducing a likelihood of the selected second detector unit contacting the subject. Once the surfaces of the selected second detector unit has been conformed to the threshold distance from the estimated outer perimeter, method 900 may proceed to 980 to determine whether the selected second detector unit is a last detector unit in the detector array (e.g., 106) to be positioned. If the selected second detector unit is not the last detector unit, method 900 may return to 935 to select another detector unit for positioning.

If the selected detector unit (e.g., 114b) is the last detector unit, the detector units may be considered in position for optimal imaging. Thus, during the NM imaging scan, the incoming radiation may pass through, and be narrowed by, the collimators (e.g., 122) associated with the various detector units. The incoming radiation may be passed to respective CZT modules (e.g., 204) such that, at 985, the NM imaging data may be acquired. Method 900 may then end.

However, returning to 945, if the selected detector unit is the first detector unit (e.g., 114a), in some examples, since portions of the estimated outer perimeter may lie within an actual perimeter of the subject (e.g., 110), the selected first detector unit may attempt to move to a position which may result in the detector unit contacting the subject, possibly causing the subject discomfort and subjecting the various components of the selected first detector unit to undue pressure. As such, proximity of the selected first detector unit to an object (e.g., the subject or another detector unit) may be detected by interruption of the LED beam (e.g., 218) projected between the pair of optical detectors (e.g., 216a, 216b) included in the selected first detector unit and remedied accordingly.

For example, at 955, method 900 may include determining whether the LED beam (e.g., 218) is obstructed by a first object. Specifically, the selected detector unit (e.g., 114a) may include two proximity detectors (e.g., 215), each proximity detector respectively including one sliding-end contact sensor (e.g., 214) and one optical sensor (e.g., 216a, 216b). The optical sensors may be disposed opposite one another, such that one of the optical sensors may generate the LED beam for the other optical sensor to receive. Obstruction of the LED beam may therefore indicate that the selected detector unit is too close to the first object, such as the subject (e.g., 110) or another detector unit.

Thus, if the LED beam (e.g., 218) is obstructed by the first object, method 900 may proceed to 960 to reverse translation of the selected detector unit (e.g., 114a) until the LED beam is unobstructed. Specifically, in examples wherein the first object is the subject (e.g., 110), the detector carrier (e.g., 116) mechanically coupled to the selected detector unit may retract the selected detector unit by a predetermined distance selected to retain high imaging resolution while minimizing discomfort to the subject and pressure applied to the selected detector unit.

If the LED beam (e.g., 218) is not obstructed by the first object, or if the selected detector unit (e.g., 114a) has been retracted by the corresponding detector carrier (e.g., 116), method 900 may proceed to 965 to determine whether the LED beam is broken as a result of contact of one of the sliding-end contact sensors (e.g., 214) with a second object. The sliding-end contact sensors may be disposed at corners adjacent to the surface (e.g., 115) of the selected detector unit facing the subject, whereby a given sliding-end contact sensor may be actuated (e.g., depressed) when the selected detector unit is pivoted toward, and then contacts, the second object. Actuation of the sliding-end contact sensor may therefore indicate that the selected detector unit is too close to the second object, such as the subject (e.g., 110) or another detector unit. In some embodiments, the second object may be different from the first object. In other embodiments, the second object may be the first object.

If the LED beam (e.g., 218) is broken as a result of contact of one of the sliding-end contact sensors (e.g., 214) with the second object, method 900 may proceed to 970 to reverse pivoting of the selected detector unit (e.g., 114a) until the sliding-end contact sensor returns to a default (e.g., unactuated and non-depressed) position. Specifically, since each sliding-end contact sensor may be mechanically coupled to one of the optical sensors (e.g., 216a, 216b), upon actuation the LED beam between the optical sensors may be broken. Reversing pivoting of the selected detector unit about a central axis thereof (e.g., the pivoting axis 324 as described above with reference to FIG. 3A) may free the sliding-end contact sensor from contact with the second object. Accordingly, the sliding-end contact sensor may return to the default position and a path of the LED beam may be restored (that is, one of the optical sensors may again receive the LED beam projected by the other optical sensor). Further, in examples wherein the second object is the subject (e.g., 110), reversing pivoting only until the sliding-end contact sensor returns to the default position may maintain a proximity of the selected detector unit to the subject, thereby retaining high imaging resolution while minimizing discomfort to the subject and pressure applied to the selected detector unit.

If the LED beam (e.g., 218) is not broken as a result of contact of one of the sliding-end contact sensors (e.g., 214) with the second object, method 900 may proceed to 975 to conform the surface (e.g., 115) of the selected detector unit (e.g., 114*a*) facing the subject (e.g., 110) to the estimated outer perimeter. Said another way, the NM imaging system (e.g., 100) may be operable to conform the selected detector unit to the estimated outer perimeter upon determination of no obstructing objects preventing such conformation.

Once the surface (e.g., 115) of the selected detector unit (e.g., 114*a*) facing the subject (e.g., 110) has been conformed to the estimated outer perimeter, or if pivoting of the selected detector unit has been reversed to return either of the sliding-end contact sensors (e.g., 214) to the default position thereof, method 900 may proceed to 980 to determine whether the selected detector unit is a last detector unit in the detector array (e.g., 106) to be positioned. If the selected detector unit is not the last detector unit, method 900 may return to 935 to select another detector unit for positioning.

If the selected detector unit (e.g., 114*a*) is the last detector unit, the detector units may be considered in position for optimal imaging. Thus, during the NM imaging scan, the incoming radiation may pass through, and be narrowed by, the collimators (e.g., 122) associated with the various detector units. The incoming radiation may be passed to respective CZT modules (e.g., 204) such that, at 985, the NM imaging data may be acquired. Method 900 may then end.

In this way, an adjustable detector array is provided for a nuclear medicine (NM) imaging system. The adjustable detector array may include a plurality of detector units, where each of the plurality of detector units may pivot and translate via respective detector carriers to conform to a patient to decrease an amount of "dead shielding" space, thereby increasing an imaging sensitivity of the NM imaging system. In some embodiments, the plurality of detector units may be disposed in an alternating configuration of larger detector units positioned outside of respective detector carriers and smaller detector units positioned within respective detector carriers. Further, each of the larger detector units may include multiple rows of cadmium zinc telluride (CZT) modules with an exchangeable collimator for acquiring imaging data (e.g., receiving photons) and each of the smaller detector units may include a single row of CZT modules with the exchangeable collimator. A technical effect of the alternating configuration is that greater imaging flexibility may be provided, where the smaller detector units may be used without the larger detector units to image small patients or regions of interest, or the smaller detector units may supplement the larger detector units in imaging large patients or regions of interest (e.g., the smaller detector units may fill in gaps between the larger detector units). Further, the exchangeable collimator may provide imaging flexibility, as different collimators may be fit to the larger detector units depending on imaging application. Additionally, each of the larger detector units may include sliding-end contact sensors paired with additional optical sensors. A technical effect of including the sliding-end contact sensors and the additional optical sensors is that the NM imaging system may detect when a given larger detector unit is within a threshold distance of the patient to be imaged, and may make corresponding adjustments to mitigate patient discomfort.

In one embodiment, a detector array comprises a plurality of adjustable imaging detectors, each of the plurality of adjustable imaging detectors comprising one of a first detector unit and a second detector unit, each first detector unit having a plurality of rows of detector modules and each second detector unit having at least one row of detector modules, where each second detector unit has fewer rows of detector modules than each first detector unit, wherein the plurality of adjustable imaging detectors are arranged on an annular gantry, the annular gantry configured for rotation about a first axis of a cylindrical aperture of the annular gantry, the first axis extending a length of the cylindrical aperture, and wherein each of the plurality of adjustable imaging detectors is disposed within the cylindrical aperture and extends orthogonally toward the first axis. In a first example of the detector array, the plurality of adjustable imaging detectors are affixed to an inner surface of the annular gantry. In a second example of the detector array, optionally including the first example of the detector array, wherein the annular gantry comprises a track circumscribed by an inner surface of the annular gantry, and the plurality of adjustable imaging detectors are positioned partially within the track such that each of the plurality of adjustable imaging detectors is operable to move independently along the track with respect to each other adjustable imaging detector. In a third example of the detector array, optionally including one or more of the first and second examples of the detector array, each of the plurality of adjustable imaging detectors comprises a telescoping detector carrier, where one of each first detector unit and each second detector unit is respectively positioned at an end of each telescoping detector carrier nearest the first axis and each telescoping detector carrier is configured to extend toward or retract from the first axis. In a fourth example of the detector array, optionally including one or more of the first through third examples of the detector array, the first axis is located at a center of the cylindrical aperture, and the annular gantry is configured for full rotation about the first axis. In a fifth example of the detector array, optionally including one or more of the first through fourth examples of the detector array, each first detector unit is configured to pivot about a second axis up to 60° from a default configuration, where each second axis is respectively located at a center of each first detector unit and each second axis is parallel with the first axis, and each second detector unit is configured to pivot about a third axis up to 90° from a default configuration, where each third axis is respectively located at a center of each second detector unit and each third axis is parallel with the first axis and each second axis. In a sixth example of the detector array, optionally including one or more of the first through fifth examples of the detector array, each detector module is a cadmium zinc telluride module. In a seventh example of the detector array, optionally including one or more of the first through sixth examples of the detector array, each first detector unit comprises three rows of detector modules, each of the three rows of detector modules comprising seven detector modules, and each second detector unit comprises only one row of detector modules, the only one row of detector modules comprising seven detector modules. In an eighth example of the detector array, optionally including one or more of the first through seventh examples of the detector array, the plurality of adjustable imaging detectors comprise six first detector units alternatingly arranged with six second detector units. In a ninth example of the detector array, optionally including one or more of the first through eighth examples of the detector array, each of the plurality of adjustable imaging detectors having the first detector unit has a same configuration as each other adjustable imaging detector having the first detector unit, and each of the plurality of adjustable imaging detectors having the second detector unit has a same configuration as each other adjustable imaging detector having the second detector unit. In a tenth example of the detector array, optionally including one or more of the first through ninth examples of the detector array, each first detector unit comprises a pair of proximity detectors disposed opposite to one another, a first one of the pair of proximity detectors comprises a first optical sensor configured to project a light-emitting diode (LED) beam, a second one of the pair of proximity detectors comprises a second optical sensor configured to receive the LED beam, and upon interruption of the LED beam by an interfering object, the first detector unit is configured to retract and/or pivot away from the interfering object. In an eleventh example of the detector array, optionally including one or more of the first through tenth examples of the detector array, each of the pair of proximity detectors comprises a sliding-end contact sensor, and upon application of a threshold pressure to any sliding-end contact sensor by the interfering object, the LED beam is interrupted. In a twelfth example of the detector array, optionally including one or more of the first through eleventh examples of the detector array, each first detector unit and second detector unit comprises an exchangeable collimator, the exchangeable collimator selected for a particular imaging application.

In another embodiment, a medical imaging system comprises an annular gantry circumscribing a cylindrical aperture, the annular gantry configured to rotate about a central axis tracing a length of the cylindrical aperture, a detector array positioned on the annular gantry, the detector array comprising a plurality of larger detector units and a plurality of smaller detector units extending toward the central axis of the cylindrical aperture, each of the plurality of larger detector units comprising a plurality of rows of cadmium zinc telluride (CZT) modules and each of the plurality of smaller detector units comprising at least one row of CZT modules, where each smaller detector unit has fewer rows of CZT modules than each larger detector unit, and each of the CZT modules is registered with an exchangeable collimator for receiving incoming radiation from a subject positioned within the cylindrical aperture, and a processing unit configured with instructions in non-transitory memory that when executed cause the processing unit to, responsive to a size of the subject being larger than a threshold size, coordinate each of the plurality of larger detector units and the plurality of smaller detector units to move to a first position to receive the incoming radiation from the subject, and acquire medical imaging data from each of the plurality of larger detector units and the plurality of smaller detector units based on the incoming radiation, and responsive to the size of the subject being smaller than the threshold size, coordinate the plurality of smaller detector units to move to a second position to receive the incoming radiation from the subject, and acquire medical imaging data from the plurality of smaller detector units based on the incoming radiation. In a first example of the medical imaging system, the processing unit is further configured to perform an automatic body contouring routine to estimate an outer perimeter of the subject, coordinating the plurality of larger detector units comprises translating and pivoting the plurality of larger detector units toward the estimated outer perimeter, and coordinating the plurality of smaller detector units comprises translating and pivoting the plurality of smaller detector units toward the estimated outer perimeter. In a second example of the medical imaging system, optionally including the first example of the medical imaging system, each of the plurality of smaller detector units comprises only one row of CZT modules, and each of the plurality of larger detector units comprises a plurality of proximity detectors configured to, upon detecting the subject within a threshold distance of a corresponding larger detector unit, retract and/or pivot the corresponding larger detector unit away from the subject. In a third example of the medical imaging system, optionally including one or more of the first and second examples of the medical imaging system, the processing unit is further configured to determine an angular resolution of the imaging data, responsive to an insufficient angular resolution being determined and the size of the subject being larger than the threshold size, retract each of the plurality of larger detector units and the plurality of smaller detector units from the subject, rotate the annular gantry about the central axis by a resolution angle, coordinate each of the plurality of larger detector units and the plurality of smaller detector units to move to a third position to receive further incoming radiation from the subject, and acquire further imaging data from each of the plurality of larger detector units and the plurality of smaller detector units based on the further incoming radiation, and responsive to the insufficient angular resolution being determined and the size of the subject being smaller than the threshold size, retract the plurality of smaller detector units from the subject, rotate the annular gantry about the central axis by the resolution angle, coordinate the plurality of smaller detector units to move to a fourth position to receive the further incoming radiation from the subject, and acquire further imaging data from the plurality of smaller detector units based on the further incoming radiation.

In yet another embodiment, a method comprises positioning a subject within a cylindrical aperture of an annular gantry, the annular gantry configured with a plurality of imaging detectors, each of the plurality of imaging detectors comprising one of a first detector unit and a second detector unit, each first detector unit and second detector unit comprising an exchangeable collimator positioned adjacent to one or more rows of cadmium telluride zinc (CZT) modules, where each first detector unit comprises three rows of CZT modules, each second detector unit has fewer rows of CZT modules than each first detector unit, and each exchangeable collimator is configured for receiving incoming radiation from an area within the subject for each corresponding CZT module, estimating each of an outer perimeter of the subject and a size of the subject, extending one or more of the plurality of imaging detectors based on the estimated size, translating and pivoting the extended one or more imaging detectors toward the estimated outer perimeter, acquiring nuclear medicine (NM) imaging data based on the incoming radiation, and diagnosing a medical issue afflicting the area within the subject based on the NM imaging data. In a first example of the method, each second detector unit comprises only one row of CZT modules, each first detector unit comprises a pair of optical sensors projecting a light-emitting diode (LED) beam therebetween, and the method comprises, responsive to any LED beam being obstructed by the subject, translating a corresponding first detector unit away from the subject until the LED beam is unobstructed. In a second example of the method, optionally including the first example of the method, each first detector unit comprises a pair of sliding-end contact sensors respectively coupled to the pair of optical sensors, and the method comprises, responsive to any LED beam being broken as a result of one of a corresponding pair of sliding-end contact sensors being contacted by the subject, pivoting a corresponding first detector unit away from the subject until the one of the corresponding pair of sliding-end contact sensors returns to a default position.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A detector array, comprising:
   a plurality of adjustable imaging detectors, each of the plurality of adjustable imaging detectors comprising one of a first detector unit and a second detector unit, each first detector unit having a plurality of rows of detector modules and each second detector unit having at least one row of detector modules, where each second detector unit has fewer rows of detector modules than each first detector unit;
   wherein the plurality of adjustable imaging detectors are arranged on an annular gantry, the annular gantry configured for rotation about a first axis of a cylindrical aperture of the annular gantry, the first axis extending a length of the cylindrical aperture, and
   wherein each of the plurality of adjustable imaging detectors is disposed within the cylindrical aperture and extends orthogonally toward the first axis.

2. The detector array of claim 1, wherein the plurality of adjustable imaging detectors are affixed to an inner surface of the annular gantry.

3. The detector array of claim 1, wherein
   the annular gantry comprises a track circumscribed by an inner surface of the annular gantry, and
   the plurality of adjustable imaging detectors are positioned partially within the track such that each of the plurality of adjustable imaging detectors is operable to move independently along the track with respect to each other adjustable imaging detector.

4. The detector array of claim 1, wherein each of the plurality of adjustable imaging detectors comprises a telescoping detector carrier, where one of each first detector unit and each second detector unit is respectively positioned at an end of each telescoping detector carrier nearest the first axis and each telescoping detector carrier is configured to extend toward or retract from the first axis.

5. The detector array of claim 1, wherein
   the first axis is located at a center of the cylindrical aperture, and
   the annular gantry is configured for full rotation about the first axis.

6. The detector array of claim 1, wherein
   each first detector unit is configured to pivot about a second axis up to 60° from a default configuration, where each second axis is respectively located at a center of each first detector unit and each second axis is parallel with the first axis, and
   each second detector unit is configured to pivot about a third axis up to 90° from a default configuration, where each third axis is respectively located at a center of each second detector unit and each third axis is parallel with the first axis and each second axis.

7. The detector array of claim 1, wherein each detector module is a cadmium zinc telluride module.

8. The detector array of claim 1, wherein
   each first detector unit comprises three rows of detector modules, each of the three rows of detector modules comprising seven detector modules, and
   each second detector unit comprises only one row of detector modules, the only one row of detector modules comprising seven detector modules.

9. The detector array of claim 1, wherein the plurality of adjustable imaging detectors comprise six first detector units alternatingly arranged with six second detector units.

10. The detector array of claim 1, wherein
    each of the plurality of adjustable imaging detectors having the first detector unit has a same configuration as each other adjustable imaging detector having the first detector unit, and
    each of the plurality of adjustable imaging detectors having the second detector unit has a same configuration as each other adjustable imaging detector having the second detector unit.

11. The detector array of claim 1, wherein
    each first detector unit comprises a pair of proximity detectors disposed opposite to one another,
    a first one of the pair of proximity detectors comprises a first optical sensor configured to project a light-emitting diode (LED) beam,
    a second one of the pair of proximity detectors comprises a second optical sensor configured to receive the LED beam, and
    upon interruption of the LED beam by an interfering object, the first detector unit is configured to retract and/or pivot away from the interfering object.

12. The detector array of claim 11, wherein
    each of the pair of proximity detectors comprises a sliding-end contact sensor, and
    upon application of a threshold pressure to any sliding-end contact sensor by the interfering object, the LED beam is interrupted.

13. The detector array of claim 1, wherein each first detector unit and second detector unit comprises an exchangeable collimator, the exchangeable collimator selected for a particular imaging application.

14. A medical imaging system, comprising:
an annular gantry circumscribing a cylindrical aperture, the annular gantry configured to rotate about a central axis tracing a length of the cylindrical aperture;
a detector array positioned on the annular gantry, the detector array comprising a plurality of larger detector units and a plurality of smaller detector units extending toward the central axis of the cylindrical aperture, each of the plurality of larger detector units comprising a plurality of rows of cadmium zinc telluride (CZT) modules and each of the plurality of smaller detector units comprising at least one row of CZT modules, where each smaller detector unit has fewer rows of CZT modules than each larger detector unit, and each of the CZT modules is registered with an exchangeable collimator for receiving incoming radiation from a subject positioned within the cylindrical aperture; and
a processing unit configured with instructions in non-transitory memory that when executed cause the processing unit to:
responsive to a size of the subject being larger than a threshold size:
coordinate each of the plurality of larger detector units and the plurality of smaller detector units to move to a first position to receive the incoming radiation from the subject, and
acquire medical imaging data from each of the plurality of larger detector units and the plurality of smaller detector units based on the incoming radiation; and
responsive to the size of the subject being smaller than the threshold size:
coordinate the plurality of smaller detector units to move to a second position to receive the incoming radiation from the subject, and
acquire medical imaging data from the plurality of smaller detector units based on the incoming radiation.

15. The medical imaging system of claim 14, wherein the processing unit is further configured to perform an automatic body contouring routine to estimate an outer perimeter of the subject,
coordinating the plurality of larger detector units comprises translating and pivoting the plurality of larger detector units toward the estimated outer perimeter, and
coordinating the plurality of smaller detector units comprises translating and pivoting the plurality of smaller detector units toward the estimated outer perimeter.

16. The medical imaging system of claim 14, wherein each of the plurality of smaller detector units comprises only one row of CZT modules, and
each of the plurality of larger detector units comprises a plurality of proximity detectors configured to, upon detecting the subject within a threshold distance of a corresponding larger detector unit, retract and/or pivot the corresponding larger detector unit away from the subject.

17. The medical imaging system of claim 14, wherein the processing unit is further configured to:
determine an angular resolution of the imaging data;
responsive to an insufficient angular resolution being determined and the size of the subject being larger than the threshold size:
retract each of the plurality of larger detector units and the plurality of smaller detector units from the subject,
rotate the annular gantry about the central axis by a resolution angle,
coordinate each of the plurality of larger detector units and the plurality of smaller detector units to move to a third position to receive further incoming radiation from the subject, and
acquire further imaging data from each of the plurality of larger detector units and the plurality of smaller detector units based on the further incoming radiation; and
responsive to the insufficient angular resolution being determined and the size of the subject being smaller than the threshold size:
retract the plurality of smaller detector units from the subject,
rotate the annular gantry about the central axis by the resolution angle,
coordinate the plurality of smaller detector units to move to a fourth position to receive the further incoming radiation from the subject, and
acquire further imaging data from the plurality of smaller detector units based on the further incoming radiation.

18. A method, comprising:
positioning a subject within a cylindrical aperture of an annular gantry, the annular gantry configured with a plurality of imaging detectors, each of the plurality of imaging detectors comprising one of a first detector unit and a second detector unit, each first detector unit and second detector unit comprising an exchangeable collimator positioned adjacent to one or more rows of cadmium telluride zinc (CZT) modules, where each first detector unit comprises three rows of CZT modules, each second detector unit has fewer rows of CZT modules than each first detector unit, and each exchangeable collimator is configured for receiving incoming radiation from an area within the subject for each corresponding CZT module;
estimating each of an outer perimeter of the subject and a size of the subject;
extending one or more of the plurality of imaging detectors based on the estimated size;
translating and pivoting the extended one or more imaging detectors toward the estimated outer perimeter;
acquiring nuclear medicine (NM) imaging data based on the incoming radiation; and
diagnosing a medical issue afflicting the area within the subject based on the NM imaging data.

19. The method of claim 18, wherein
each second detector unit comprises only one row of CZT modules,
each first detector unit comprises a pair of optical sensors projecting a light-emitting diode (LED) beam therebetween, and
the method comprises, responsive to any LED beam being obstructed by the subject, translating a corresponding first detector unit away from the subject until the LED beam is unobstructed.

20. The method of claim 19, wherein
each first detector unit comprises a pair of sliding-end contact sensors respectively coupled to the pair of optical sensors, and
the method comprises, responsive to any LED beam being broken as a result of one of a corresponding pair of sliding-end contact sensors being contacted by the subject, pivoting a corresponding first detector unit away from the subject until the one of the corresponding pair of sliding-end contact sensors returns to a default position.

\* \* \* \* \*